(12) United States Patent
Negussie et al.

(10) Patent No.: US 11,382,990 B2
(45) Date of Patent: Jul. 12, 2022

(54) IMAGEABLE POLYMERS, METHODS OF MAKING AND METHODS OF USE THEREOF

(71) Applicant: The United States of America, as Represented by the Secretary, Department of Health and Human Services, Bethesda, MD (US)

(72) Inventors: Ayele H. Negussie, Bethesda, MD (US); Bradford Johns Wood, Bethesda, MD (US)

(73) Assignee: THE USA, AS REPRESENTED BY THE SECRETARY, DHHS, Beth, MD (US)

( * ) Notice: Subject to any disclaimer, the term of this patent is extended or adjusted under 35 U.S.C. 154(b) by 0 days.

(21) Appl. No.: 16/349,458

(22) PCT Filed: Oct. 31, 2017

(86) PCT No.: PCT/US2017/059406
§ 371 (c)(1),
(2) Date: May 13, 2019

(87) PCT Pub. No.: WO2018/093566
PCT Pub. Date: May 24, 2018

(65) Prior Publication Data
US 2020/0197540 A1    Jun. 25, 2020

Related U.S. Application Data

(60) Provisional application No. 62/422,972, filed on Nov. 16, 2016, provisional application No. 62/459,242, filed on Feb. 15, 2017.

(51) Int. Cl.
*A61K 49/04*    (2006.01)

(52) U.S. Cl.
CPC ................ *A61K 49/0419* (2013.01)

(58) Field of Classification Search
None
See application file for complete search history.

(56) References Cited

U.S. PATENT DOCUMENTS

| | | |
|---|---|---|
| 2003/0120355 A1 | 6/2003 | Hafeli et al. |
| 2004/0258614 A1 | 12/2004 | Line et al. |
| 2006/0067883 A1 | 3/2006 | Krom et al. |

FOREIGN PATENT DOCUMENTS

| | | |
|---|---|---|
| EP | 0259096 A1 | 3/1988 |
| WO | 198702893 A1 | 5/1987 |
| WO | 199003036 A1 | 3/1990 |
| WO | 2004071495 A1 | 8/2004 |
| WO | 2005061009 A2 | 7/2005 |
| WO | 2008034911 A1 | 3/2008 |
| WO | 2014159759 A1 | 10/2014 |
| WO | 2015033092 A1 | 3/2015 |
| WO | 2015033093 A1 | 3/2015 |

OTHER PUBLICATIONS

Hruby et al. Lutetium-177 and iodine-131 loaded chelating polymer microparticles intended for radioembolization of liver malignancies. 2011 React. Funct. Polym. 71: 1155-1159. (Year: 2011).*
Ali et al. Input of Isosteric and Bioisosteric Approach in Drug design. 2014 Journal of the Chemical Society of Pakistan 36: 150-169. (Year: 2014).*
Drahos et al.; "Synthesis of a Versatile Building Block Combining Cyclen-derivative DO3A with a Polyamine via a Rigid Spacer"; Molecules; 18; pp. 13940-13956; (2013).
Dreher et al.; "Radiopaque Drug-Eluting Beads for Transcatheter Embolotherapy: Experimental Study of Drug Penetration and Coverage in Swine"; J. Vasc Interv Radiol. 23(2); pp. 257-264; (2012).
Forster et al.; "Comparison of DC Bead-irinotecan and DC Bead-topotecan Drug Eluting Beads for Use in Locoregional Drug Delivery to Treat Pancreatic Cancer"; J. Mater Sci: Mater Med; 21; pp. 2683-2690; (2010).
International Search & Written Opinion; International Publication No. PCT/US2017/059406; International Filing Date Oct. 31, 2017; dated Feb. 16, 2018; 15 pages.
Lewis et al.; "Doxorubicin Eluting Beads—1: Effects of Drug Loading on Bead Characteristics and Drug Distribution" J Mater Sci: Mater Med; 18; pp. 1691-1699; (2007).
Mandai et al.; "Direct Thrombosis of Aneurysms With Cellulose Acetate Polymer"; J. Neurosurg; 77; pp. 497-500; (1992).
Morrison et al.l; "Synthesis and Characterization of Polystyrene Embolization Particles Doped with Tantalum Oxide Nanoparticles for X-ray Contract"; J. Matter Sci: Mater Med; 26;218; pp. 1-14; (2015).
Sung et al.; "Multimetallic Complexes and Functionalized Gold Nanoparticles Based on a Combination of d- and f-Elements"; Inorg. Chem. 53; pp. 1989-2005; (2014). Wibowo et al.; "Novel Bismuth and Lead Coordination Polymers Cynthesized With Pyridine-2,5-Dicarboxylates: Two Single Component "White" Light Emitting Phosphors"; Inorg. Chem.; 49; pp. 11001-11008, (2010).
Yang et al.; "Synthesis and Structural Characterization of Complexes of a DO3A-Conjugated Triphenylphosphonium Cation With Diagnostically Important Metal Ions"; Inorg Chem.; 46(21); pp. 8988-8997; (2007).

\* cited by examiner

*Primary Examiner* — Jennifer Lamberski
(74) *Attorney, Agent, or Firm* — McBee Moore & Vanik IP, LLC

(57) ABSTRACT

Described herein are X-ray imageable polymers such as polymeric particles comprising bismuth as a radiopacifying agent, methods of making the polymers, and methods of using the polymers. The imageable particles may comprise a covalently bound compound which chelates the bismuth, for example, through a combination of nitrogen and oxygen atoms.

21 Claims, 8 Drawing Sheets

IMAGEABLE POLYMERS, METHODS OF MAKING AND METHODS OF USE THEREOF

CROSS REFERENCE TO RELATED APPLICATIONS

This application is a National Stage application of PCT/US2017/059406, filed on Oct. 31, 2017, which claims the benefit of U.S. Provisional Application Nos. 62/422,972 filed on Nov. 16, 2016 and 62/459,242 filed on Feb. 15, 2017, all of which are incorporated by reference in their entirety herein.

FIELD OF THE DISCLOSURE

The present disclosure is related to imageable polymers, methods of making the polymers, and methods of using the polymers such as in imaging and in loco-regional drug delivery.

BACKGROUND

Therapeutic transarterial embolization has been used as a loco-regional therapy treatment modality for various lesions for more than four decades. It combines blood vessel occluding embolic materials to starve the tumor as well as cytotoxic drugs for therapeutic tumor killing. In 1968, the first embolic material that was successfully used to treat spinal-cord arteriovenous malformation was a stainless steel plate. In the late 1970's, this technique was used to control local growth of an unresectable liver tumor by obliterating the blood supply feeding the tumor. This therapy has gained momentum and many randomized clinical trials have been conducted since 1974. Advances in materials science and engineering have enabled diverse technologies that aid the physician to perform better loco-regional treatments. The advent of advanced micro catheter technology and drug-eluting particles, also known commonly as Drug Eluting Beads (DEBs) for trans arterial chemoembolization (TACE), for instance, has improved patient survival by decreasing complication rates as compared to conventional TACE (cTACE).

Drug eluting particles are novel devices as well as drug delivery vehicles for loco-regional therapy particularly in patients with unresectable hepatocellular carcinoma (HCC). These particles are made of inert elastic materials with hydrophilic properties and spherical geometry. The particle size may be tailored to embolize different size vessels. The particles are typically compressible so that the particles pass through a micro-catheter to the distal vessels without clumping to achieve targeted occlusion. In addition, the particles may be coated, for instance with polyphosphazene, to modify the surface properties. The use of drug eluting particles as loco-regional therapy has become increasingly important for patients with HCC because of these advances in technology (microcatheter technology, precisely tailored microspheres and imaging technology), survival benefit, and a favorable safety profile. Although curative measures, such as liver transplantation and surgical resection, continue to be the gold standard for the treatment of HCC, approximately 70% to 80% of patients are poor candidates for such invasive procedures. Advanced liver cirrhosis, stage of disease at presentation, and multiple illnesses limit patients from curative intervention. These patients often have extrahepatic spread of disease, cancer-related symptoms, and portal vein invasion, warranting alternative approaches that may help decrease rates of disease progression and recurrence. The only technique available for such patients is TACE.

Historically, TACE includes injection of chemotherapeutic drugs with or without Lipiodol® into the hepatic artery, followed by administration of embolizing agents. With the advancement of technology, new embolizing agents such as DEBs with drug loading and releasing capabilities have emerged in clinics. The use of DEBs has been shown to significantly reduce liver toxicity and systemic drug exposure compared to cTACE. Therefore, TACE with DEBs has been shown to be effective in prolonging survival in comparison to standard supportive care in randomized controlled trials and meta-analyses.

A major hurdle, however, is the inability to visualize the embolic material during and post treatment, particularly in determining locations of the injection and the optimal end-point of the treatment. These limitations cause major procedural variability between physicians who are involved in carrying out TACE procedures. In commercially available imageable particles, the radiopacity (radiodensity) is derived from covalently attached iodinated species. These iodinated particles are more dense compared to the equivalent non iodinated particles hence their suspensions may sediment more quickly. These iodinated particles are also less compressible, limiting their administration using microcatheters. Furthermore, as the X-ray density is due to the presence of iodine, it is difficult to distinguish between the iodinated particles and the soluble iodinated contrast agents commonly employed in embolization procedures.

What is needed are novel imageable particles that may be visualized and differentiated by X-Ray, for example by multispectral CT or photon counting CT, for example, in the presence of other clinical contrast agents, such as those containing iodine. Further, it would be useful to provide particles that have a density and/or compressibility comparable to conventional embolic particles.

BRIEF SUMMARY

In an aspect, an X-ray imageable polymer, particularly a polymeric particle, comprises bismuth as a radiopacifying agent. In an aspect, the bismuth is bound to the polymer in the form of a complex comprising the bismuth, such as bismuth complexed with a complexing molecule, e.g., a chelating molecule. The chelating molecule may itself be covalently coupled to the polymer, optionally via a linker.

In another aspect, the X-ray imageable polymer comprises a polymer having covalently bound thereto a compound of Formula (1):

$$\text{BiQ-A-L[G-*]}_n \qquad \text{Formula (1)}$$

wherein Q is a complexing molecule; Bi is a bismuth ion coordinated to the complexing molecule; A is covalent bond or a functional group; L is a $C_1$-$C_{30}$ linking group optionally containing one or more nitrogen, oxygen or sulphur atoms, or a combination of oxygen, nitrogen and sulfur atoms; or taken together A and L are a bond linking Q to G; G is a residue of a functional group; n is an integer corresponding to one less than the valence of L, and is 1 to 6; and *is a point of covalent attachment to the polymer.

In a further aspect, the X-ray imageable polymer comprises a polymer having covalently bound thereto a compound of Formula (2) or Formula (3),

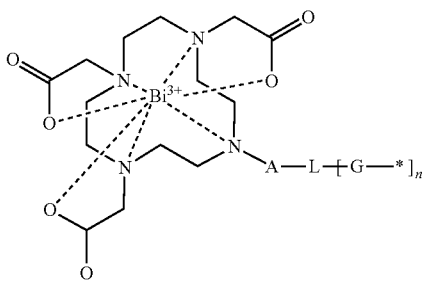

Formula (2)

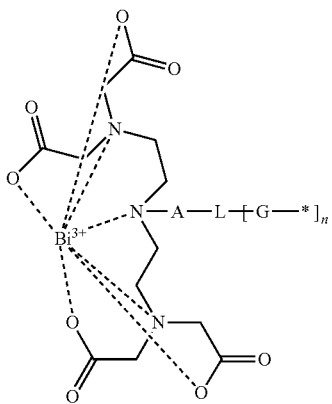

Formula (3)

wherein A, L, G, n and *are as defined above.

In another aspect, a process for making an X-ray imageable polymer comprises reacting a precursor polymer with a compound of Formula (4)

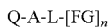
Q-A-L-[FG]$_n$      Formula (4)

under conditions effective to covalently bind the compound of Formula (4) to the precursor polymer and provide a modified polymer, wherein FG is a functional group reactive with a functional group of the precursor polymer, and adding a bismuth compound to the modified polymer under conditions effective to chelate the bismuth compound to the covalently bound compound of Formula (4) to provide the X-ray imageable polymer.

In yet another aspect, a method of making an X-ray imageable polymer comprises reacting a precursor polymer with a complex of Formula (7)

BiQ-A-L-[FG]$_n$      Formula (7)

under conditions effective to covalently bind the compound of Formula (7) or to the precursor polymer to provide the x-ray imageable polymer.

In a further aspect, an imaging method comprises intravascularly (intraarterially or intravenously) administering the X-ray imageable particles described herein and imaging the X-ray imageable particles in the vessel (artery or vein) of the subject, for example using an X-ray based technique.

In a further aspect, a method of treating a subject having a tumor comprises intravascularly (intraarterially or intravenously) administering to an artery of the tumor the X-ray imageable particles described herein, and imaging the particles in the blood vessel (vein or artery) of the subject. The particles may additionally comprise an active pharmaceutical agent wherein the reversibly bound active agent may be released from the polymer or particles into the blood vessel (vein or artery).

Figure 1:
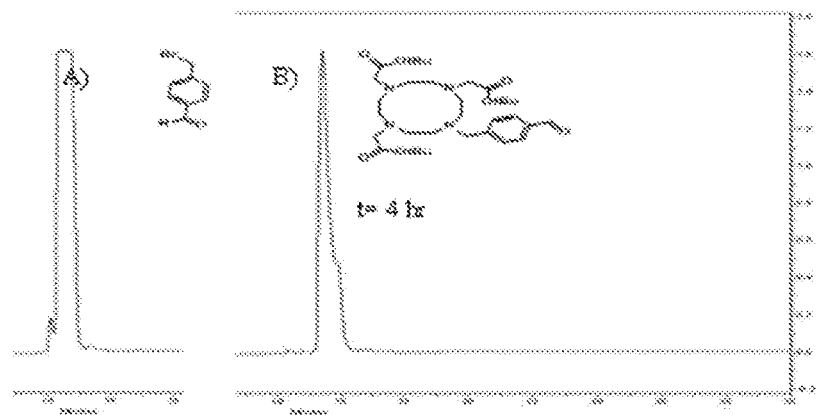
FIG. 1 is an HPLC profile of reactant (4-(bromomethyl) benzaldehyde) and product.

The above-described and other features will be appreciated and understood by those skilled in the art from the following detailed description, drawings, and appended claims.

DETAILED DESCRIPTION

Described herein are novel X-ray imageable bismuth-containing polymers, particularly polymeric particles, methods of making the polymers, methods of using the polymers and articles and compositions comprising the polymers. The present inventors have identified that it is possible to prepare polymers, e.g., polymeric particles, comprising bismuth as an imageable agent. The bismuth is particularly useful as a radiopacifying agent (radiopacifier). These bismuth-containing polymers are useful in procedures in which the polymer is to be imaged within the body, such as by X-ray, for example in therapeutic embolization procedures. They are particularly useful in procedures in which the polymer is differentiated under X-ray from an iodine-containing agent, such as an iodinated polymer or iodine containing contrast agent, as discussed further below.

A variety of polymers that comprise a chelating functionality have been proposed; such polymers are discussed, for example, in WO2008/034911A1, US2004/0258614A1, US2006/0067883A1 WO1987/002893A1 and WO2014/159759.

An X-ray imageable polymer, which may be in the form of particles such as microspheres, comprises bismuth as an imageable agent. An imageable agent is an agent that renders the polymer imageable within the body by an imaging technology, such as X-ray, thus bismuth is a radiopacifying agent. The bismuth may be incorporated into the polymer for example as dispersed particles or in the form of a bismuth compound in an insoluble form such as a powder. A bismuth salt, which is insoluble or sparingly soluble in water, such as bismuth oxide bismuth nitrate, bismuth hydroxide, bismuth subgallate, bismuth subcitrate, and bismuth subsalicylate may be used.

In a particularly preferred aspect, the bismuth is bound to the polymer in the form of a complex, such as a complex with a complexing molecule, which may itself be covalently coupled to the polymer, optionally via a linking group. The complexing agent may have one or more nitrogen, oxygen, or sulfur atoms that chelate the bismuth, such as three or four nitrogen atoms, three or four oxygen atoms, and optionally one sulphur atom.

The complexing molecule may be linked to the polymer by a bond, or by a linking group -A-L- or -L- as described below.

As used herein an X-ray imageable polymer is a polymer comprising bismuth as described herein. In an aspect, the polymer comprises a complexing molecule that is covalently bound to the polymer and chelated or complexed with bismuth.

In an aspect the X-ray imageable polymer is of the Formula (1):

  Formula (1)

wherein
Q is a complexing molecule;
Bi is a bismuth ion coordinated to the complexing molecule;
A is covalent bond or a functional group coupling the complexing molecule to the linker;
L is a $C_1$-$C_{30}$ linking group optionally containing one or more nitrogen, oxygen or sulphur atoms, or a combination of oxygen, nitrogen and sulfur atoms; or taken together A and L are a bond linking Q to G;
G is a residue of a functional group;
n is an integer corresponding to one less than the valence of L, and is 1 to 6; and
*is a point of covalent attachment to the polymer.

In preferred aspects, less than 50% of the bismuth present is unchelated, and preferably less than 25%, more preferably less than 10%, and most preferably less than 5% of the bismuth present is in unchelated form.

The bismuth containing polymers described herein comprise bismuth at a level sufficient to render them imageable by X-ray, i.e. sufficient to render them radiopaque. The bismuth used to render the polymer imageable is naturally occurring bismuth and is non-radioactive, that is, it is generally not enriched in any bismuth isotope greater than that found naturally. Thus the particles typically comprise no unstable medical bismuth isotopes, such as $^{212}$Bi, $^{213}$Bi, and $^{206}$Bi.

The amount of bismuth in the polymer depends on the level of radiodensity required. The X-ray imageable polymers may comprise at least 10 mg of bismuth per cm$^3$ of polymer, preferably 25 mg per cm$^3$ of polymer, more preferably at least 40 mg per cm$^3$ of polymer, and especially at least 65 mg per cm$^3$ of polymer, wherein when the polymer comprises chelated bismuth, the minima preferably refer to the chelated compound.

The quantity of bismuth in the X-ray imageable polymer may be at least 10% wt/wt, preferably at least 20% wt/wt, more preferably at least 30% wt/wt and most preferably at least 35% wt/wt, based on the polymer dry weight.

Preferably, the X-ray imageable polymer has a radiodensity of at least 500 HU, preferably at least 1500 HU, more preferably at least 2500 HU, and particularly at least 3900 HU. HU is measured at 65 kV, for example, according to example 15.

The complexing molecule Q is capable of complexing bismuth. A complexing molecule is capable of binding with bismuth through single or multiple sites. These sites have lone pairs of electrons which may be donated to the d orbitals of the bismuth, forming coordination bonds. An exemplary complexing molecule is a chelating molecule. A chelating molecule may bind to a single bismuth ion through several atoms present in the molecule. These atoms have lone pairs which may donate to the empty d orbitals of the bismuth. Thus, chelating agents are multidentate ligands.

The complexing molecule Q may be a chelating molecule. The chelating molecule may have three or four nitrogen atoms and three oxygen atoms which chelate the bismuth. The chelating molecule may have three or four oxygen atoms, optionally three or four nitrogen atoms, and further optionally one or more sulphur atoms, which chelate the bismuth. In an aspect, the chelating molecule has three or four oxygen atoms, three or four nitrogen atoms, and optionally one sulphur atom which chelate the bismuth. In a further aspect, the chelating molecule has three oxygen atoms that chelate the bismuth. The chelating molecule preferably has three or four nitrogen atoms and three oxygen atoms. The bismuth is preferably fully co-ordinated.

Exemplary complexing molecules include alkylenediamine-N,N,N',N'-tetraacetic acids, such as ethylene diamine tetraacetic acid (EDTA); ethylene glycol-bis(β-aminoethyl ether-N,N,N',N'-tetraacetic acid (EGTA), cyclohexanediaminetetraacetic acid (CDTA); 1,4,7,10-tetra-azacylododecane N,N,N'',N'''-tetraacetic acid (DOTA), diethylenetriaminepentaacetic acid (DTPA), diethylenetriamine-N1,N2,N3,N3-tetraacetic acid (DTTA), tetraazacyclododecane-1,4,7,10-tetraacetic acid (DO3A), 1,4,7-triazacyclononane-triacetic acid (NOTA), 1,4,7-triazacyclononane-1-succinic acid-4, 7-diacetic acid (NODASA), 1,4,7-triazacyclononane, 1-glutaric acid-4,7-acetic acid (NODAGA), mercaptoacetyltriglycine (MAG3) or MAG3 derivatives; N-(2-acetamido)iminodiacetic acid (ADA), 2,3-dimercapto-1-propanesulfonic acid (DMPS); meso-2,3-dimercaptosuccinic acid (DMSA); crown ethers such as benzo-18-crown-6, 12-crown-4 and 18-crown-6-; pentetic acid; 4-hexadecyl-2, 2, 9, 9-tetramethyl-4, 7-diaza-1, 10-decanedithiol (HOD); ethylcysteinate dimer; and a bis(diethyldithiocarbamato) nitrido(DEDC) chelator; salicylate, thiosalicylate, amino salicylate, gallate, and citrate.

Preferably the chelating molecule is salicylate, gallate, amino salicylate, citrate, DOTA or DTPA.

The functional group A may be, for example, a covalent bond or —O—, —S—, —C(=O)—, —OC(=O)—, —C(=O)O—, —NR$^{20}$—, —C(=O)N(R$^{21}$)—, =N—, —N=N—, —S(=O)$_2$—, —N=, or —N=N$^+$=N$^-$, ˆ—(CH$_2$)$_p$C(=O)NH—, ˆ—(CH$_2$)$_p$C(=O)NHC(=O)—, ˆ—(CH$_2$)$_p$OC(=O)—, ˆ—(CH$_2$)$_p$C(=O)O—, ˆ—(CH$_2$)$_p$NH—, ˆ—(CH$_2$)$_p$N=, ˆ—(CH$_2$)$_p$N=N—, or ˆ—(CH$_2$)$_p$NHC(=O)O—, wherein ˆ indicates a bond to the nitrogen; where R$^{20}$ and R$^{21}$ are independently H or $C_1$-4 alkyl; and p is 1 to 6.

The functional group A is preferably a covalent bond, —O—, —S—, —C(=O)—, —OC(=O)—, —C(=O)O—, —NR$^{20}$—, —C(=O)N(R$^{21}$)—, —S(=O)$_2$—ˆ—(CH$_2$)$_p$C(=O)NH—, ˆ—(CH$_2$)$_p$C(=O)NHC(=O)—, ˆ—(CH$_2$)$_p$OC(=O)—, ˆ—(CH$_2$)$_p$C(=O)O—, ˆ—(CH$_2$)$_p$NH—, ˆ—(CH$_2$)$_p$N=, ˆ—(CH$_2$)$_p$N=N—, or ˆ—(CH$_2$)$_p$NHC (=O)O—, wherein ˆ indicates a bond to the nitrogen; where $R^{20}$ and $R^{21}$ are independently H or $C_{1-4}$ alkyl; and p is 1 to 6.

The functional group A is more preferably a covalent bond, —O—, —S—, —C(=O)—, —OC(=O)—, —C(=O)O—, —$NR^{20}$—, —S(=O)$_2$—, ˆ—(CH$_2$)$_p$C(=O)NH—, ˆ—(CH$_2$)$_p$C(=O)NHC(=O)—, ˆ—(CH$_2$)$_p$C(=O)—, ˆ—(CH$_2$)$_p$C(=O)O—, ˆ—(CH$_2$)$_p$NH— or ˆ—(CH$_2$)$_p$NHC(=O)O—, wherein ˆ indicates a bond to the nitrogen; where $R^{20}$ is H or $C_1$-4 alkyl; and p is 1 to 6.

The chelating molecule may be linked to the polymer by a linking group, L. In an aspect, L is a $C_1$-$C_{30}$ linking group optionally containing one or more nitrogen, oxygen or sulphur atoms, or a combination of oxygen, nitrogen, and sulfur atoms; or taken together A and L are a bond linking Q to G. The linking group may comprise a polyethylene glycol (PEG) chain having from 1 to 15 ethylene glycol units, preferably 1 to 10 ethylene glycol units, and most preferably 1 to 6 ethylene glycol units. In another aspect the linking group comprises 1 to 8 atoms that may be oxygen, nitrogen, or sulfur. The linking group may be a $C_{1-12}$ linking group.

In an embodiment, L is a $C_{1-12}$ linking group. More specifically, L is a linking group having a valence of n+1, and is a $C_{1-10}$ alkyl, $C_{2-10}$ alkenyl, $C_{2-10}$ alkynyl, $C_{6-10}$ aryl, $C_{3-11}$ heteroaryl, $C_{7-12}$ arylalkyl, $C_{7-12}$ alkylaryl, $C_{5-10}$ cycloalkyl, or $C_{3-9}$ heterocycloalkyl. In some embodiments, L is optionally substituted with a functional groups such as an aldehyde, azide, alkyne, carboxylic acid, amine, acid halide, anhydride, or ester.

Particularly preferred L include $C_{1-10}$, especially $C_{1-6}$ alkylene or methylene; phenylene; $C_{1-4}$ alkyl-phenylene, especially methyl-phenylene; and phenyl-$C_{1-4}$ alkylene, especially phenyl-methylene or a PEG chain of from 1 to 6 ethylene glycol units.

In some aspects, L is optionally substituted with a functional group such as an aldehyde, azide, alkyne, carboxylic acid, amine, acid halide, anhydride, nitro, hydroxyl, $C_{1-10}$ alkoxy, halogen (F, Cl, Br or I), thiol, thioether $C_{1-4}$ alkyl or ($C_{1-10}$ alkyl)ester.

Preferably, where L is substituted, the substituents are selected from aldehyde, carboxylic acid, amine, nitro, hydroxyl, $C_{1-6}$ alkoxy, halogen (F, Cl, Br or I), thiol, thioether, $C_{1-4}$ alkyl, or ($C_{1-6}$ alkyl) ester.

Where the linker is substituted by nitro, substitution is preferred to be on an aryl group, where present, since this leads to colored products useful in visualizing the polymer. In some aspects, A and L taken together form a bond linking Q directly to G.

The group G is a residue of a functional group, and is —O—, —S—, —C(=O)—, —OC(=O)—, —C(=O)O—, —NH—, =N—, —N=N—, or —S(=O)$_2$—. In a specific aspect, n is 1-3. Particularly G is —O—, —OC(=O)—, —C(=O)O— and —NH, such that the linker is coupled to the polymer through an ether, ester, amine, or cyclic acetal group.

A wide variety of polymers are appropriate for use in the X-ray imageable polymers. Preferably the polymer is a hydrophilic polymer, which may be cross-linked physically or covalently. Preferably the polymer is water-swellable but water-insoluble, and may comprise greater than 50% and up to 99% water, as a hydrogel.

In an aspect, the polymer comprises groups carrying positive and/or negative charges, such that it is able to bind compounds carrying the opposite charge at physiological pH (pH 7.4). A variety of charged groups may be used, including sulphonate and carboxylate groups.

The polymer may have a molecular weight of 2,000 to 500,000 grams per mole (g/mol), or 5,000 to 200,000 g/mol, or 10,000 to 100,000 g/mol. Such weights are exemplary.

Exemplary polymers include acrylates (including $C_{1-10}$ alkyl esters or their salts), acrylamides, acrylics, acetals, allyls, polysaccharides, methacrylates (including $C_{1-10}$ alkyl esters or their salts), methacrylics, methacrylamides, polyalkylene glycols, polyamides, polycarbonates, polyesters, polyethers, polyimides, polyetherimides, polyolefins, polypeptides, polyphosphates, polyurethanes, silicones, styrenics, vinyls, or combinations or copolymers thereof. Preferably the polymer is formed from monomers such as: vinyl alcohols, polyethylene glycols, polypropylene glycols, acrylates (including $C_{1-6}$ alkyl esters or their salts), methacrylates (including $C_{1-6}$ alkyl esters or their salts), acrylamides, methacrylamides, lactates, glycolates, or a combination comprising at least one of the foregoing.

Exemplary hydrophilic polymers include polyvinyl alcohol, polyvinyl acetal, ($C_{1-6}$ alkyl) acrylates, acrylate salts, ($C_{1-6}$ alkyl) methacrylates, methacrylate salts, carboxymethylcellulose, hydroxyethylcellulose, polyacrylic acid, polymethacrylic acid, polymethylmethacrylate, polyvinylpyrrolidone, polyacrylamide, polyethylene glycol (PEG), PEG-methacrylate, PEG-methylmethacrylate, tris(hydroxymethyl)methyl]acrylamide, N,N-methylene-bis-acrylamide, poly(DL-lactide-co-glycolide), polylactate, polyglycolate, chitosan, alginate, gelatin, starch, or a combination or co-polymer comprising at least one of the foregoing. Such polymers may be crosslinked either covalently or physically. The salt counterion may be any suitable counterion, for example sodium, potassium, ammonium, or pyridyl.

In a particular aspect, the polymer comprises a polyhydroxy polymer such as polyvinyl alcohol or co-polymers and mixtures thereof. These polymers may be cross linked either covalently or physically. A specific polyvinyl alcohol polymer or particle comprises a PVA hydrogel modified with sulphonate groups. A specific example of such a polymer comprises a PVA macromer with N-acryloylaminoacetaldehyde (NAAADA), cross linked with 2-acrylamido-2-methylpropane sulfonic acid (AMPS) (as described in US20070258939).

In an aspect, the polymer is in the form of a particle. The polymer particles are typically microspheres having an average largest diameter of up to 2000 μm, such as 30 to 200 μm, although the actual size ranges used will depend inter alia on the clinical need. Such particles may be prepared in any sub size range required, by sieving. Typical size ranges include 100-300, 300-500, 500-700 and 700-900 μm, although smaller size ranges may be advantageous in some circumstances due inter alia, to their more distal embolization properties. Such smaller size ranges include 70-150 or 40 to 90 μm. Typically sizes less than 20 μm are generally avoided due to off target embolizations due to passage through the capillary bed, thus a lower practical limit is 30 μm. Sizes in the range 40 to 700 μm, preferably 40 to 300 μm most commonly used in clinical practice. Particles may be substantially spherical particles, known as microspheres, but may have varying degrees of polydispersion.

In an aspect, an X-ray imageable bismuth polymer or particle comprises a covalently bound compound of Formula (2) or Formula (3), or BiQ-A-L-[G-*]$_n$, wherein BiQ is bismuth subsalicylate, bismuth subgallate, or bismuth subcitrate,

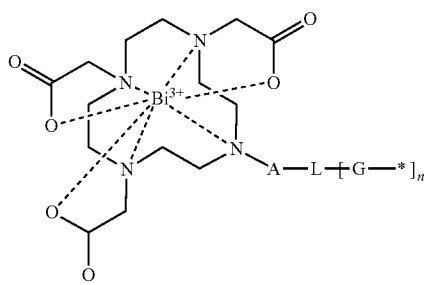

Formula (2)

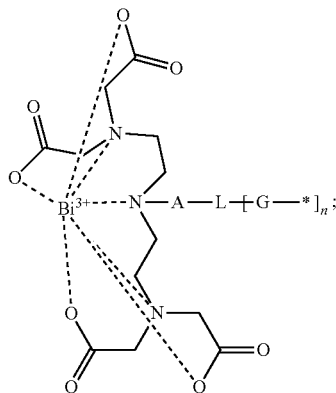

Formula (3)

or
wherein A, L, G, n and *are as defined above.

In an aspect, the ratio of the polymer to the compound of Formula (2) or Formula (3) is 0.1:1 to 1:1 (wt/wt).

In formulas (2) and (3) A is a covalent bond, —O—, —S—, —C(=O)—, —OC(=O)—, —C(=O)O—, —NR$^{20}$—, —S(=O)$_2$—, ˆ—(CH$_2$)$_p$C(=O)NH—, ˆ—(CH$_2$)$_p$C(=O)NHC(=O)—, ˆ—(CH$_2$)$_p$O C(=O)—, ˆ—(CH$_2$)$_p$C(=O)O—, ˆ—(CH$_2$)$_p$NH— or ˆ—(CH$_2$)$_p$NHC(=O)O—, wherein ˆ indicates a bond to the nitrogen; where R$^{20}$ is H or C$_{1-4}$ alkyl; and p is 1 to 6

Further in formulas (2) and (3) L is substituted or unsubstituted and is n+1, and is a C$_{1-10}$ alkyl, C$_{2-10}$ alkenyl, C$_{2-10}$ alkynyl, C$_{6-10}$ aryl, C$_{3-11}$ heteroaryl, C$_{7-12}$ arylalkyl, C$_{7-12}$ alkylaryl, C$_{5-10}$ cycloalkyl, or C$_{3-9}$ heterocycloalkyl. In some aspects, L is optionally substituted with a functional groups such as those listed above for L and an aldehyde, azide, alkyne, carboxylic acid, amine, acid halide, anhydride, or ester.

Also in formulas (2) and (3), G is a residue of a reactive group, including —O—, —S—, —C(=O)—, —OC(=O)—, —C(=O)O—, —NH—, =N—, —N=N—, or —S(=O)$_2$—, and n is 1-3.

In an aspect, the chelating molecule complexing bismuth (BiQ-) is bismuth subsalicylate, bismuth thiosalicylate, bismuth aminosalicylate, bismuth subcitrate or bismuth subgallate, preferably bismuth subsalicylate or subgallate, which in a preferred aspect, may be coupled through the phenyl ring. The group A is then considered to be the group directly coupled to the phenyl ring.

In the case of these complexing molecules, the preferred functional groups A are a covalent bond, —O—, —S—, —C(=O)—, —OC(=O)—, —C(=O)O—, —NR$^{20}$— or —C(=O)N(R$^{21}$)—, and particularly a covalent bond, —C(=O)—, —OC(=O)—, —C(=O)O— or —C(=O)N(R$^{21}$)—; wherein R$^{20}$ and R$^{21}$ are independently selected from H and C$_{1-4}$ alkyl.

L is particularly optionally substituted C$_{1-6}$ alkylene, such as ethylene or methylene; phenylene; C$_{1-4}$ alkyl-phenylene, especially methyl-phenylene; and phenyl-C$_{1-4}$ alkylene, especially phenyl-methylene and G is —O—, —OC(=O)—, —C(=O)O— and —NH, such that the linker is coupled to the polymer through an ether, ester, amine or cyclic acetal group;

Alternatively A and L taken together are a bond coupling the chelating or complexing group directly to G.

In a more specific aspect, the covalently bound compound is of Formula (2a) or Formula (3a)

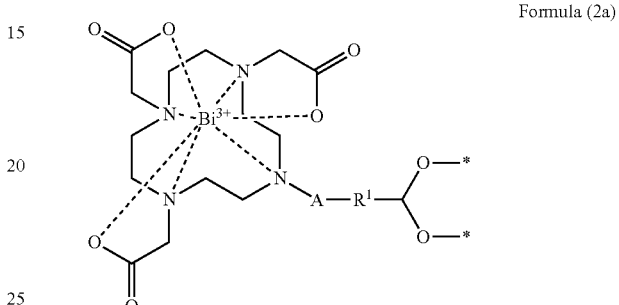

Formula (2a)

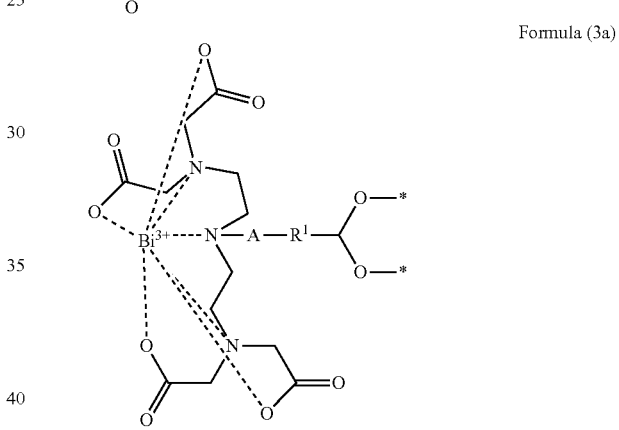

Formula (3a)

or is a compound of the formula (30)

Formula (30)

wherein BiQ is bismuth subsalicylate, bismuth sulphosalicylate, bismuth aminosalicylate, bismuth subcitrate, or bismuth subgallate, particularly bismuth subsalicylate or subgallate.

The group R$^1$ is a covalent bond or a substituted or unsubstituted C$_{1-12}$ divalent linking group. The above groups are particularly suited for coupling to polyhydroxylated polymers, such as those having 1,2 or 1,3 dihydroxy groups such as those found in PVA or polymers comprising PVA.

In Formulas (2a) and (3a), and (30), for example, R$^1$ is substituted or unsubstituted and is C$_{1-10}$ alkylene, C$_{2-10}$ alkenylene, C$_{6-10}$ arylene, C$_{3-11}$ heteroarylene, C$_{7-12}$ alkylenearylene, C$_{7-12}$ arylenealkylene, C$_{5-10}$ cycloalkylene, or C$_{3-9}$ heterocycloalkylene, or PEG having 1 to 6 ethylene glycol units.

More specifically, A is a covalent bond, —C(=O)—, C(=O)O— or —CH₂C(=O)O—, and R¹ is a substituted or unsubstituted $C_{1-10}$ alkylene, $C_{6-10}$ arylene, or $C_{7-12}$ alkylenearylene. Preferred R¹ groups and their substituents are as defined for L.

Particularly for formula (30), A is a covalent bond, —O—, —S—, —OC(=O)—, —C(=O)O—, —NR²⁰— and —C(=O)N(R²¹)—, and particularly a covalent bond, —C(=O)—, —OC(=O)—, C(=O)O— and —C(=O)N(R²¹)—; wherein R²⁰ and R²¹ are independently selected from H and $C_{1-4}$ alkyl; and R¹ is preferably an optionally substituted $C_{1-6}$ alkylene, such as ethylene or methylene; phenylene; $C_{1-4}$ alkyl-phenylene, especially methyl-phenylene; and phenyl-$C_{1-4}$ alkylene, especially phenyl-methylene. More specifically, R¹ is substituted or unsubstituted and is $C_{1-6}$ alkylene, $C_{6-10}$ arylene, or $C_{7-12}$ alkylenearylene.

Alternatively A and R¹ taken together are a bond.

Exemplary compounds of Formulas (2), (3) and (30) include the following:

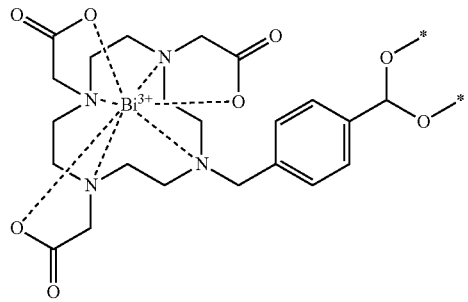

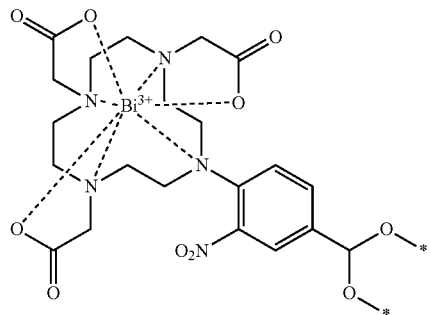

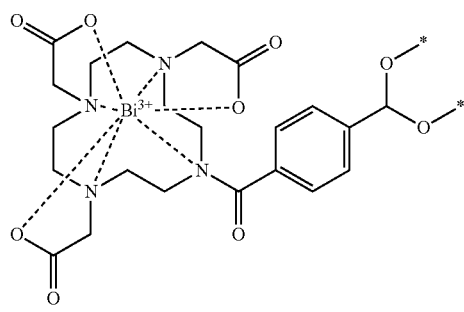

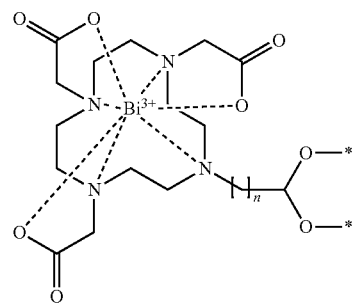

wherein n is 1 to 10,

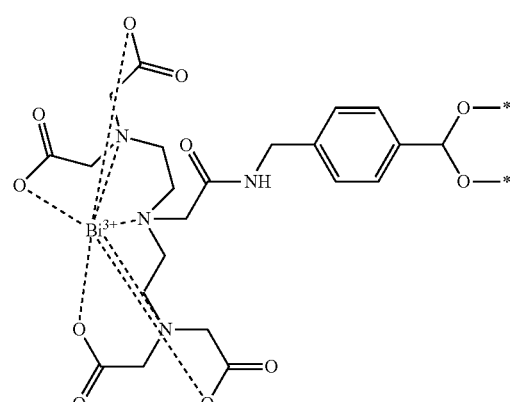

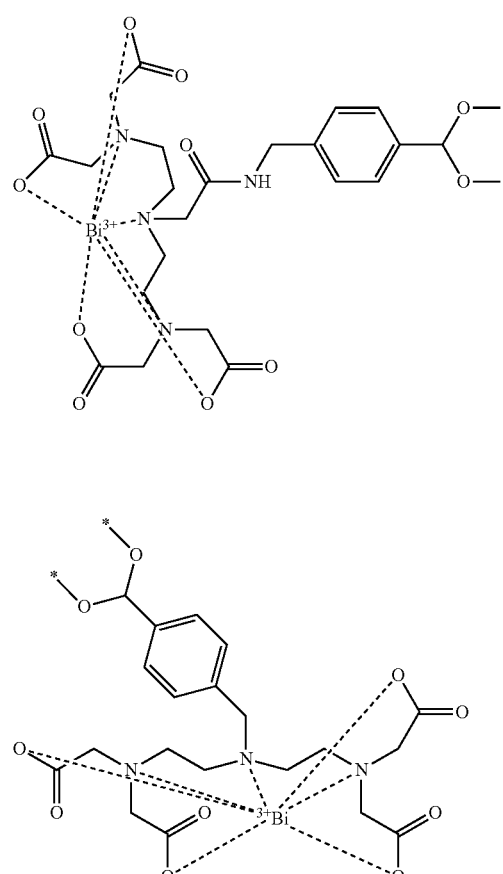

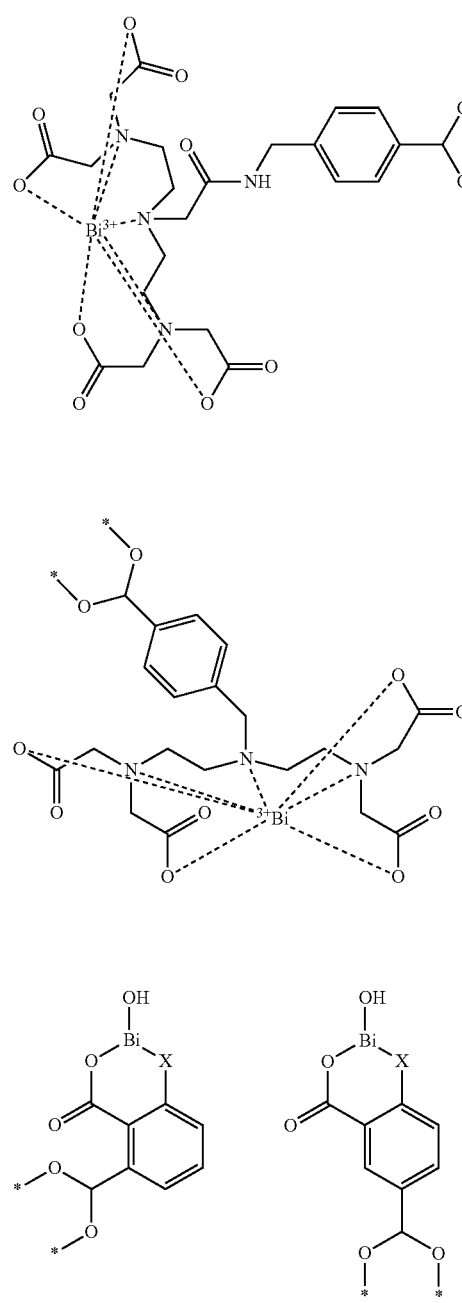

-continued

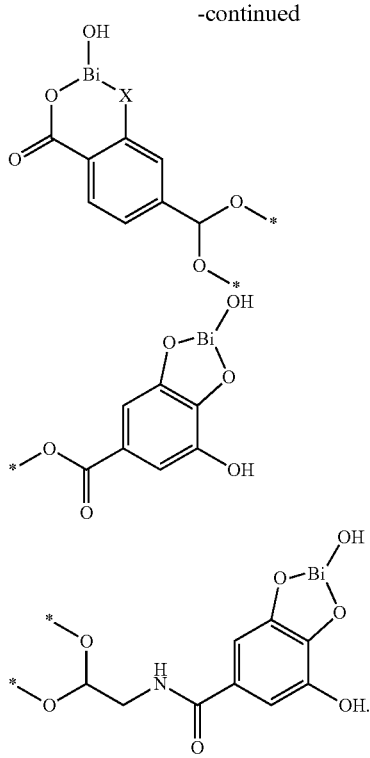

X = O, S or NH

When the compound of Formula (2a), Formula (3a), or Formula (30) is one of the immediately preceding compounds, the polymer preferably comprises polyvinyl alcohol, polyvinyl acetal, carboxymethylcellulose, hydroxyethylcellulose, polyacrylic acid, polyvinylpyrrolidone, polyacrylamide, poly(DL-lactide-co-glycolide), chitosan, alginate, or a combination comprising at least one of the foregoing.

The imageable bismuth polymers optionally further comprise a reversibly bound active agent, preferably a chemotherapeutic agent, an antibody, an antibody fragment, a peptide, a low molecular weight protein, or a combination thereof. Exemplary chemotherapeutic agents include doxorubicin, daunarubicin, epirubicin, irinotecan, cisplatin, mitomycin C, 5-fluorouracil, topotecan, sorafenib, sutent (sunitinib, and vandetinib, small molecules, peptides, antibodies, antibody fragments, or any combination thereof. Additional exemplary therapeutic agents include cetuximab, trastuzimab, nivolumab, TLR agonists, immunomodulatory agents, checkpoint inhibitors, anti-CTLA4 ab, Anti-PD1, anti-PD-L1ab, imatinib, and the like. Such compounds may be used in their ionic forms as salts.

Reversibly bound agents may be bound within the polymer by ionic interaction, such as by interaction with positively or negatively charged groups of the polymer as described herein. Such groups will be charged at physiological pH (pH 7.4) and include, for example, carboxylate or sulphonate groups.

In a specific aspect, the polymer is in the form of polymeric microspheres. A pharmaceutical composition comprises the X-ray imageable polymer in the form of microspheres, and a pharmaceutically acceptable diluent or carrier. The pharmaceutical composition may be in dried form and held under a vacuum of less than 0.1 atmosphere until use.

In a first aspect, a method of making the X-ray imageable polymer described herein comprises reacting a precursor polymer with a compound of the formula Q-A-L-[FG]$_n$     Formula (4)

under conditions effective to covalently bind the compound of Formula (4) to the precursor polymer and provide a modified polymer, wherein Q, A and L are as defined above, and FG is a functional group reactive with a functional group of the polymer precursor; and adding a bismuth compound to the modified particle under conditions effective to chelate the bismuth compound to the covalently bound compound of Formula (4) to provide the X-ray imageable polymer.

Suitable reaction conditions effective to covalently bind the compound of Formula (4) to the precursor polymer and provide a modified polymer depend on the particular functional group FG and the reactive group of the polymer, and are known to those of ordinary skill in the art. For example, when FG is an aldehyde group and the polymer precursor contains reactive hydroxyl groups, acetalization conditions can be used (e.g., stirring in the presence of an acid catalyst). When FG is a carboxylic acid group and the polymer precursor contains reactive hydroxyl groups, esterification conditions (e.g., stirring in the presence of an acid, basic, or metal alkoxide catalyst) may be used. Alternatively if FG is a hydroxyl group and the polymer precursor contains reactive carboxyl groups, the same conditions can be used. Other conditions, such as amidation conditions are known. The reactions may generally be carried out at room temperature or above (e.g., 21-100° C.) in a solvent. Polar aprotic solvents may be used, for example dimethyl sulfoxide (DMSO), dimethyl formamide (DMF) or tetrahydrofuran (THF).

Suitable conditions effective to chelate the bismuth compound to the covalently bound compound of Formula (4) include combining the compound of formula (4) and the bismuth compound. For example, the compound of formula (4) and the bismuth compound can be combined in a solvent at room temperature or elevated temperature (e.g., 21-200° C. or 50-150° C.). The solvent is selected to allow dissociation of the bismuth compound (if a salt), and can be a protic solvent (e.g., water, methanol, ethanol, propanol, or the like) or a polar aprotic solvent (e.g., DMSO, DMF, or THF. In an aspect the bismuth compound is a salt, and the solvent is water, optionally adjusted to a pH effective to dissociate the salt (e.g., a pH of 7-11, or 8-10, or 8-9).

In a specific aspect, the compound of the formula (4) is a cyclen compound of Formula (5) or an azanyl compound of Formula (6)

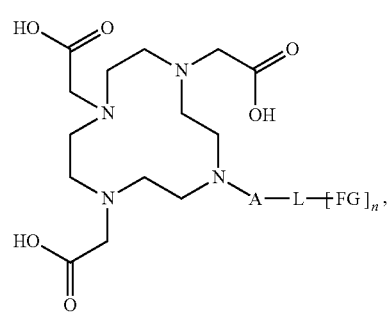

Formula (5)

Formula (6)

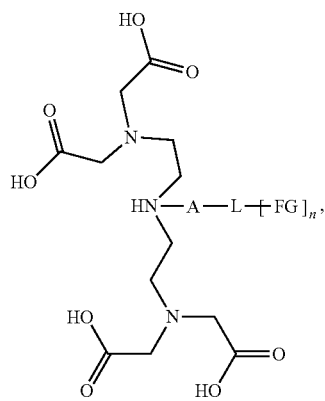

Formula (6a)

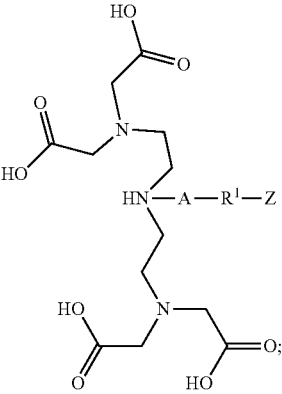

or a compound of the Formula (4) wherein Q is a salicylate, sulphosalicylate, citrate or gallate group.

In the above aspects of making the X-ray imageable polymer, FG is, for example, isocyanato, azido, halogen, nitrile, hydroxyl, or —C(=O)Y wherein Y is a hydrogen, halogen, or —OR wherein R is a hydrogen or a leaving group; and the functional group of the polymer precursor is, for example, —OH, —NH$_2$, —SH, or —C(=O)OH.

In further specific aspect, the compound of the formula (4) is a compound of the Formula (10)

Q-A-L-Z                                                 Formula (10)

wherein Z is of the formula

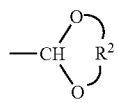

wherein $R^2$ is a $C_{5-6}$ alkylene, or —C(=O)Y wherein Y is a hydrogen, halogen, or —OR wherein R is a hydrogen or a leaving group.

In a more specific aspect, the compound of the formula (10) is a cyclen compound of Formula (5a) or the azanyl compound of Formula (6a)

Formula (5a)

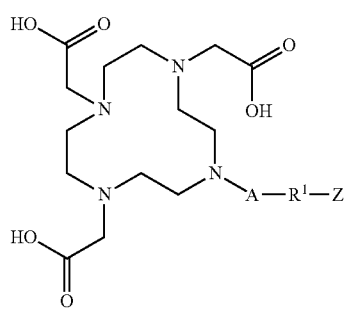

or is a compound of the formula (10) wherein Q is a salicylate, citrate or gallate group.

In another aspect, making the X-ray imageable polymer described herein comprises reacting a precursor polymer with a bismuth complex of Formula (7)

BiQ-A-L-[FG]$_n$                                 Formula (7)

under conditions effective to covalently bind the bismuth complex of Formula (7) to the precursor polymer to provide the X-ray imageable polymer, wherein Q, A, L, and FG are as defined above.

As described above, suitable reaction conditions effective to covalently bind the compound of Formula (7) to the precursor polymer and provide a modified polymer depend on the particular functional group FG and the reactive group of the polymer, and are known to those of ordinary skill in the art. To prevent loss of bismuth from the complex, the reactions may be performed using a basic catalyst, where possible. For example, when FG is an aldehyde group and the polymer precursor contains reactive hydroxyl groups, acetalization conditions can be used (e.g., stirring in the presence of a metal-containing catalyst). When FG is a carboxylic acid group and the polymer precursor contains reactive hydroxyl groups, esterification conditions (e.g., stirring in the presence of a basic or metal alkoxide catalyst) may be used. Alternatively if FG is a hydroxyl group and the polymer precursor contains reactive carboxyl groups, the same conditions can be used. Other conditions, such as amidation conditions are known. The reactions may generally be carried out at room temperature or above (e.g., 21-100° C.) in a solvent. Polar aprotic solvents may be used, for example DMSO, DMF, or tetrahydrofuran THF.

In a specific second aspect, the bismuth complex of the formula (7) is a bismuth-cyclen complex of Formula (8), a bismuth-azanyl (e.g., DTPA) complex of Formula (9)

Formula (8)

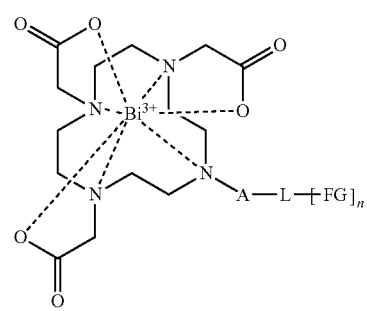

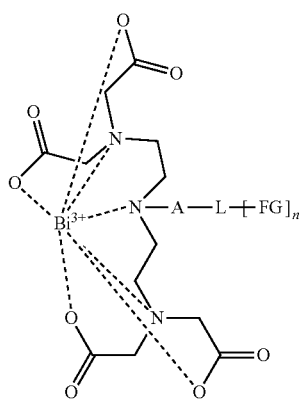

Formula (9)

or a compound of the Formula (7) wherein BiQ is bismuth subsalicylate, bismuth sulphosalicylate, bismuth subcitrate or bismuth subsalicylate.

In the above aspects of making the X-ray imageable polymer, FG is, for example, isocyanato, azido, halogen, nitrile, hydroxyl, or —C(=O)Y wherein Y is a hydrogen, halogen, or —OR wherein R is a hydrogen or a leaving group; and the functional group of the polymer precursor is, for example, —OH, —NH$_2$, —SH, or —C(=O)OH.

In a further specific aspect, the bismuth complex of the formula (7) is a compound of the formula (11)

BiQ-A-L-Z                    Formula (11)

wherein Z is of the formula

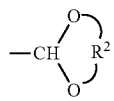

wherein R$^2$ is a C$_{5-6}$ alkylene, or —C(=O)Y wherein Y is a hydrogen, halogen, or OR wherein R is a hydrogen or a leaving group.

In a more specific aspect of the second method of making an imageable bismuth particle, the bismuth complex of the formula (11) is a bismuth cyclen complex is of Formula (8a) or a bismuth azanyl complex is of Formula (9a)

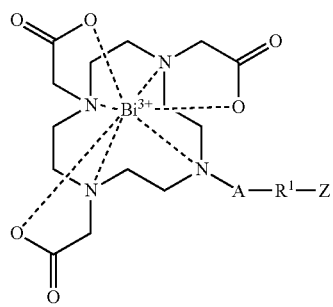

Formula (8a)

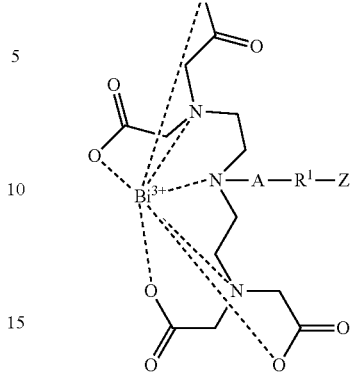

Formula (9a)

In any of the foregoing aspects, Z may be —C(=O)H and the reacting with the hydrophilic polymer precursor may comprise acetalizing hydroxyl groups of the hydrophilic polymer precursor.

In certain aspects, the compound of Formula (5) is produced by reacting a compound of Formula (12)

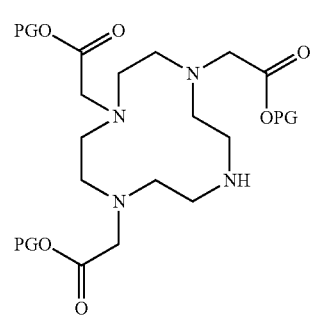

Formula (12)

wherein PG is hydrogen or a protecting group, with a compound of Formula (13) or Formula (14)

W-L-FG                    Formula (13)

W-L-PFG                    Formula (14)

wherein W is a functional group reactive with a secondary amine and PFG is a protected functional group; and deprotecting the groups PG and the groups PFG where the compound of Formula (14) is reacted. In this and other aspects, functional groups W reactive with secondary amines are known, and include for example various halides (preferably C$_1$ or Br), aldehydes, anhydrides, carbonyl halides, carboxylic acids, thioacids, and the like. Reaction conditions for such nucleophilic substitutions are known. Preferably the functional group is a halide.

The compound of Formula (13) or Formula (14) may be a compound of one or more of the formulas

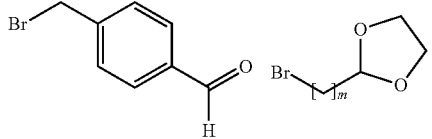

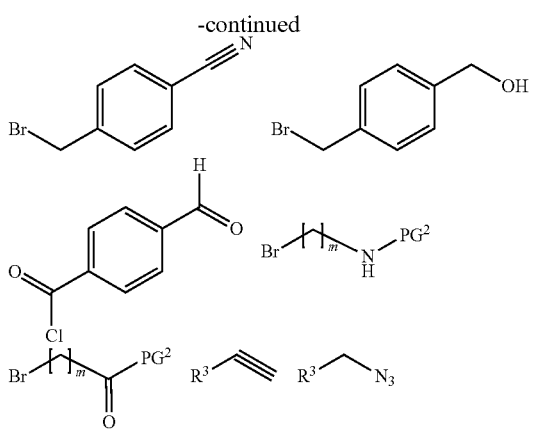

wherein PG² is a protecting group, m is an integer of 1-30, or 1-12, or 1-6, and R³ is a $C_{1-36}$ moiety containing a functional group reactive with a secondary amine, preferably a $C_{1-36}$ alkyl halide, or $C_{6-36}$ aromatic halide. In an aspect, m is an integer of 1-12, 1-6, or 1-4 and R³ is a $C_{1-36}$ alkyl halide or $C_{6-36}$ aromatic halide.

The compound of Formula (5) wherein A is a covalent bond may be made by reacting a compound of Formula (15) or Formula (16)

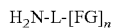            Formula (15)

$H_2N-L-[FG]_n$

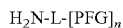            Formula (16)

$H_2N-L-[PFG]_n$ wherein PFG is a protected functional group, with a compound of Formula (17)

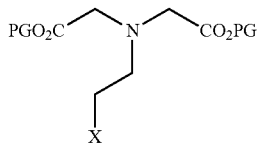

Formula (17)

wherein PG is hydrogen or a protecting group and X is a halogen; and deprotecting the groups PG and the group PFG where the compound of Formula (16) is reacted.

The compound of Formula (6) wherein A is functional group may be made by reacting a compound of Formula (18) or Formula (19)

            Formula (18)

$U-L-[FG]_n$

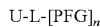            Formula (19)

$U-L-[PFG]_n$ with a compound of Formula (20)

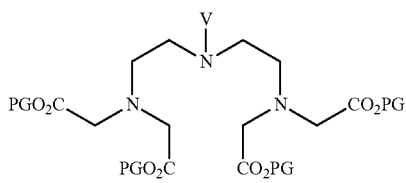

Formula (20)

wherein PFG is a protected functional group, PG is a hydrogen or a protecting group, and U is a group reactive with V to form the functional group A; and deprotecting the groups PG and the group PFG where the compound of Formula (19) is reacted. Functional groups U and V suitable for reaction to form functional group A are known, and include V being an aldehyde and U being a carboxylic acid, as described in L. Bannwart, S. Abele, S. Tortoioli, *Synthesis*, 2016, 48, 2069-2078.

The compound of Formula (8) may be produced by reacting a compound of Formula (12)

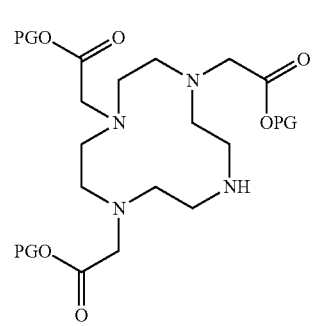

Formula (12)

wherein PG is hydrogen or a protecting group, with a compound of Formula (13) or Formula (14)

            Formula (13)

W-L-FG

            Formula (14)

W-L-PFG wherein W is a functional group reactive with a secondary amine as described above and PFG is a protected functional group; deprotecting the groups PG and the groups PFG where the compound of Formula (14) is reacted, to provide the compound of Formula (5); and adding a bismuth compound to the compound of Formula (5) under conditions effective to chelate the bismuth compound to provide the compound of Formula (8).

The compound of Formula (13) or Formula (14) may be a compound of one or more of the formulas

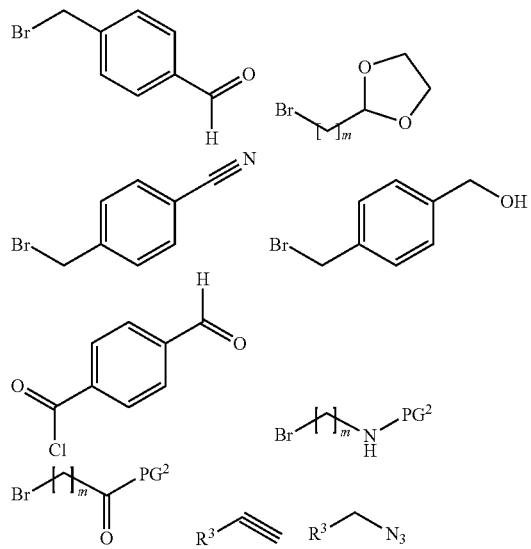

wherein PG² is a protecting group, m is an integer of 1-30 or 1-12, or 1-6, and R³ is a $C_{1-36}$ moiety containing a functional group reactive with a secondary amine, preferably a $C_{1-36}$ alkyl halide, or $C_{6-36}$ aromatic halide. In an aspect, m is an integer of 1-12, 1-6, or 1-4 and $R^3$ is a $C_{1-36}$ alkyl halide or $C_{6-36}$ aromatic halide.

The compound of Formula (9) wherein A is a covalent bond may be produced by reacting a compound of Formula (15) or Formula (16)

$$H_2N-L-[FG]_n \quad \text{Formula (15)}$$

$$H_2N-L-[PFG]_n \quad \text{Formula (16)}$$

wherein PFG is a protected functional group, with a compound of Formula (17)

[Formula (17): structure with PGO$_2$C–CH$_2$–N(–CH$_2$CO$_2$PG)–CH$_2$CH$_2$–X]

wherein PG is hydrogen or a protecting group and X is a halogen; and deprotecting the groups PG and the group PFG where the compound of Formula (16) is reacted to provide the compound of Formula (6); and adding a bismuth compound to the compound of Formula (6) under conditions effective to chelate the bismuth compound to provide the compound of Formula (9).

The compound of Formula (9) wherein A is functional group may be produced by reacting a compound of Formula (14) or Formula (15)

$$U-L-[FG]_n \quad \text{Formula (18)}$$

$$U-L-[PFG]_n \quad \text{Formula (19)}$$

with a compound of Formula (20)

[Formula (20): structure with central N–V group, with PGO$_2$C and CO$_2$PG substituents]

wherein PFG is a protected functional group, PG is a hydrogen or a protecting group, U is a group reactive with V to form the functional group A; and deprotecting the groups PG and the groups PFG where the compound of Formula (16) is reacted, to provide the compound of Formula (6); and adding a bismuth compound to the compound of Formula (6) under conditions effective to chelate the bismuth compound to provide the compound of Formula (9).

Exemplary bismuth compounds for use in any of the foregoing methods include triphenyl bismuth, $Bi(CF_3SO_3)_3$, $Bi(NO_3)_3$, $BiCl_3$, $Bi(O)ClO_4$, bismuth citrate, bismuth iodide, bismuth (III) acetate, bismuth (III) oxychloride, bismuth (III) gallate, $BiPh_3$, or a combination comprising any one or more of the foregoing. $Bi(CF_3SO_3)_3$ is generally preferred.

In the foregoing aspects, the compound of Formula (5a) may be produced by reacting a compound of Formula (12)

[Formula (12): macrocyclic structure with PGO, OPG, NH groups]

wherein PG is hydrogen or a protecting group, with a compound of Formula (16)

$$X-A-R^1-Y \quad \text{Formula (21)}$$

wherein X is a halogen and Y is a group of the formula Z or a protected carbonyl group; deprotecting the groups PG; and where Y is a protected carbonyl group, converting the group Y to the group of the formula Z.

The compound of Formula (21) may be a compound of one or more of the formulas

[Structures shown: Br–CH$_2$–C$_6$H$_4$–CHO; Br–(CH$_2$)$_m$–CH(O–CH$_2$–CH$_2$–O) acetal; OHC–C$_6$H$_4$–C(=O)Cl; Br–(CH$_2$)$_m$–C(=O)–PG$^2$]

wherein $PG^2$ is a protecting group, and m is an integer of 1-30, or 1-12, or 1-6. In an aspect, m is an integer of 1-12, or 1-6, or 1-4.

The compound of Formula (6a) wherein A is a covalent bond may be produced by reacting a compound of Formula (22)

$$H_2N-R^1-Y \quad \text{Formula (22)}$$

wherein Y is a group of the formula Z or a protected carbonyl group, with a compound of Formula (17)

[Formula (17): structure with PGO$_2$C–CH$_2$–N(–CH$_2$CO$_2$PG)–CH$_2$CH$_2$–X]

wherein PG is hydrogen or a protecting group and X is a halogen; and deprotecting the groups PG; and where Y is a protected carbonyl group, converting the group Y to the group of the formula Z.

The compound of Formula (6a) wherein A is functional group may be produced by reacting a compound of Formula (23)

$$U-R^1-Y \quad \text{Formula (23)}$$

with a compound of Formula (20)

Formula (20)

wherein PG is a hydrogen or a protecting group, and U is a group reactive with V as described in formula (18) and (19) to form the functional group A; deprotecting the groups PG; and where Y is a protected carbonyl group, converting the group Y to the group of the formula Z.

The compound of Formula (8a) may be produced by reacting a compound of Formula (12)

Formula (12)

wherein PG is hydrogen or a protecting group, with a compound of Formula (21)

$$X\text{-}A\text{-}R^1\text{—}Y \quad \text{Formula (21)}$$

wherein X is a halogen and Y is a group of the formula Z or a protected carbonyl group; deprotecting the groups PG; where Y is a protected carbonyl group, converting the group Y to the group of the formula Z to provide the compound of Formula (5a); and adding a bismuth compound to the compound of Formula (5a) under conditions effective to chelate the bismuth compound to provide the compound of Formula (6a).

The compound of Formula (21) may be a compound of one or more of the formulas wherein $PG^2$ is a protecting group and m is an integer of 1-30 or 1-12, or 1-6. In an aspect, m is an integer of 1-12, 1-6, or 1-4.

The compound of Formula (9a) wherein A is a covalent bond may be produced by reacting a compound of Formula (22)

$$H_2N\text{—}R^1\text{—}Y \quad \text{Formula (22)}$$

wherein Y is a group of the formula Z or a protected carbonyl group, with a compound of Formula (17)

Formula (17)

wherein PG is hydrogen or a protecting group and X is a halogen; and deprotecting the groups PG, and where Y is a protected carbonyl group, converting the group Y to the group of the formula Z to provide the compound of Formula (6a); and adding a bismuth compound to the compound of Formula (6a) under conditions effective to chelate the bismuth compound to provide the compound of Formula (9a).

The compound of Formula (9a) wherein A is functional group may be produced by reacting a compound of Formula (23)

$$U\text{—}R^1\text{—}Y \quad \text{Formula (23)}$$

with a compound of Formula (20)

Formula (20)

wherein PFG is a protected functional group, PG is a hydrogen or a protecting group, W is a group reactive with V to form the functional group A, and where Y is a protected carbonyl group, converting the group Y to the group of the formula Z to provide the compound of Formula (6a); and adding a bismuth compound to the compound of Formula (6a) under conditions effective to chelate the bismuth compound to provide the compound of Formula (7a).

Optionally, the deprotecting and the converting are in the same step in any of the foregoing aspects.

In any of the foregoing aspects, the bismuth compound is triphenyl bismuth, $Bi(CF_3SO_3)_3$ or $Bi(NO_3)_3$. $BiCl_3$, $Bi(O)ClO_4$, bismuth citrate, bismuth iodide, bismuth (III) acetate, bismuth (III) oxychloride, bismuth (III) gallate, $BiPh_3$, or a combination comprising one or more of the foregoing. $Bi(CF_3SO_3)_3$ is preferred.

The imageable bismuth polymers provided herein make available a variety of new products and methods of treatment.

In an aspect, the X-ray imageable polymer may be used to make imageable polymer articles that are imageable inside the body, using X-ray imaging, such as CT and micro CT imaging, so that in an aspect, provided herein is an article, such as an implantable device, imageable inside the body of a patient by X-ray comprising an X-ray imageable polymer as described herein. Such articles may comprise the polymers in the form of an imageable coating for example, or the article may comprise or consist essentially of the polymer, such as in the case of imageable embolic devices such as microspheres; stents, sutures, closures, gauzes, catheters, vascular grafts and other polymer devices.

The X-ray imageable polymers, particularly X-ray imageable particles, described herein may be used in methods of treatment by therapeutic embolization. Many such methods are now known. Therapeutic embolization may be used to slow down or stop bleeding, for example in the gut, or during surgical procedures, or such approaches may be used to reduce or stop the blood supply to areas of tissue or to tissues such as hypervascular tumors. Thus, in an aspect, a method of treatment comprises administering the X-ray imageable particles described herein, e.g., in the form of microspheres, to a blood vessel feeding a tissue of a subject, and imaging the imageable particles in the blood vessel of the subject. Intravascular administration may be performed using a catheter (e.g., a microcatheter). Such protocols may be used in the treatment of hyper vascular tumors such as hepatocellular carcinoma (HCC) by delivering the particles to blood vessels supplying the tumor. Alternatively, the method may be used to treat benign tumors or hyperplasias such as benign prostate hyperplasia or uterine fibroids, or in procedures to induce weight loss, such as gastric artery embolization.

The X-ray imageable particles described herein may be used in intravascular (e.g., intraarterial) imaging and/or treatment methods such as TACE. Thus, in an aspect, an imaging method comprises intravascularly (intraarterially or intravenously) administering X-ray imageable particles described herein to a subject, and imaging the X-ray imageable particles in a vessel, e.g. an artery, of the subject. Intraarterial administration may be performed using a catheter (e.g., a microcatheter).

In an aspect, the methods are used to image a tumor, or to image the position of polymer articles such as particles within the tumor. An interventional radiologist, for example, will locate a main artery or vein feeding a tumor, and then use a guidewire to position a microcatheter into the vessel which is used to intravascularly (intraarterially or intravenously) administer the imageable bismuth particles. Optionally, the X-ray imageable particles are administered in a contrast agent comprising iodine, such as liquid iodine. Advantageously, the X-ray imageable particle and the iodine contrast agent may be differentiated using imaging methods such as dual energy computed tomographic (CT) imaging.

Imaging the X-ray imageable particles may include dual-energy CT or photon counting CT. In X-ray CT, materials having different elemental compositions may be represented by identical pixel values on a CT image (i.e., CT numbers), depending on the mass density of the material. Materials having different elemental compositions may be represented by the same, or very similar, CT numbers, making the differentiation and classification of different types of tissues extremely challenging. In dual-energy CT, an additional attenuation measurement is obtained at a second energy, allowing the differentiation of the two materials.

In a dual-energy CT system, anatomy is exposed to two different ranges of photon energy (e.g., a low range and a high range). Each image shows a portion of anatomy exposed to one of the two different ranges of the photon energy. Data (e.g., luminance intensities of pixels corresponding to materials in the anatomy exposed to the two energy ranges) acquired from each image is typically displayed using a 2D scatter plot. The 2D plot is used to distinguish between different materials in anatomy exposed to the low energy range and high energy range.

The use of energy-resolving photon-counting detectors offers another solution. In a quad energy photon counting CT system, for example, anatomy is exposed to four different ranges of photon energy. For example, each range of photon energy may be equal to or less than one of four different energy threshold values and the pixels in each image correspond to the anatomy exposed to one of the four different ranges of photon energy. It is difficult to visually display pixel data (e.g., luminance intensity of pixels) corresponding to different materials in anatomy exposed to the four different energy ranges such that the different materials are easily distinguishable.

A photon counting detector may offer several advantages over dual-energy CT systems. Dual-energy X-ray systems typically have less efficient energy integrating detectors, requiring high radiation dose levels which limits their use for serially evaluating a soft tissue, such as an atherosclerotic plaque. In contrast, a photon counting detector may provide enough information to characterize components of a soft tissue, and, because of their high detection efficiency, may be operated at relatively low dose levels to allow safe repeated studies of the same subject. In some aspects, the detector is a CdTe photon counting detector, such as CdTe radiation line sensor.

In an aspect, the X-ray imageable particles may be used in a treatment method such as a TACE procedure to treat a tumor, such a hypervascular tumor. In a typical two-step prior art TACE procedure, an emulsion containing a chemotherapeutic agent is intravascularly (intraarterially or intravenously) administered, followed by administration of an embolic agent such as gelatin foam or a microparticulate material. The embolic agent blocks the artery and reduces loss of the chemotherapeutic agent. In an aspect, the X-ray imageable particles may be used as the embolic agent in a two-step procedure.

More recently, DEBs have been developed for use in one-step TACE procedures. In a one-step TACE procedure, the particle comprises the chemotherapeutic agent. When the DEB is intravascularly (intraarterially or intravenously) administered, the drug is released from the particle while the particle provides embolization. Such procedures reduce the inter-procedure variability of the two-step procedure. However, in general, the currently available radiodense DEBs include iodine which makes them visible by X-ray and CT scans, however, the particles are typically administered in the presence of iodine solution, which is used as a contrast agent. Thus, early in administration, it is difficult to distinguish the particles from the contrast agent. The X-ray imageable particles described herein provide a distinct advantage because the particle will be separately detectable from the iodine contrast liquid.

In an aspect, X-ray imageable polymers and particles comprise a reversibly bound active agent, preferably a chemotherapeutic agent, an antibody, an antibody fragment, a peptide, a low molecular weight protein, or a combination thereof. Once intravascularly (intraarterially or intravenously) administered, the X-ray imageable particles may be imaged in the artery of the subject.

In an aspect, a method of treating a subject having a tumor comprises intravascularly (intraarterially or intravenously) administering to an artery of the tumor the X-ray imageable particles described herein, and imaging the X-ray imageable particles in the artery of the subject, wherein the reversibly linked chemotherapeutic agent is released from the particles into the artery.

Exemplary chemotherapeutic agents that may be reversible linked to the particles include doxorubicin, irinotecan, cisplatin, mitomycin C, 5-fluorouracil, or any combination thereof.

Although the liver is a common target for TACE, other organs, including, but not limited to, the pancreas, lung, kidney, prostate, stomach, colon and head and neck have been treated using these methods. In an aspect, the subject has intermediate stage hepatocellular carcinoma.

The X-ray imageable polymers, for example, may be used to make implants or to coat implants, for example. Liquid polymers may be used to seal wounds and then vizualise the polymer sealant in situ.

The invention is further illustrated by the following non-limiting examples.

EXAMPLES

Methods

All reagents were purchased from commercial sources and used without further purification.

Samples were monitored by reverse-phase HPLC using a Beckman system Gold HPLC (Fullerton, Calif.) equipped with a 126 solvent module and 168 UV detector ($\lambda$=254 nm) controlled by 32 Karat software and Beckman Ultrasphere™ $C_{18}$ column (ODS, 4.6×250 mm, 5 μm). The flow rate was 1 mL/min and the mobile phase was isocratic with 90% A (0.1% TFA in water) and 10% B (0.1% TFA in acetonitrile) at 0-5 min, followed by a gradient eluent going from 10% B at 5 min to 90% B at 15 min. The mobile phase was then isocratic with 90% B at 15-25 min.

TLC was carried out on Merck silica gel 60 TLC plates $F_{254}$ and visualized by UV at 254 nm. Column chromatography was performed using silica gel 60 (70-230 mesh). $^1$H and $^{13}$C were NMR recorded on a Bruker Avance™ 300 instrument and using deuterated solvent. Mass spectra were recorded with a Waters (Waltham, Mass. USA) LCT Premiere™ ESI TOF mass spectrometer. The instrument was operated in positive ion ESI mode at a mass resolution of 10,000. Accurate masses were determined using the internal standard method.

Particle washing:
1. Water soluble portion: wash with water
2. Water insoluble particulates: the reaction condition produces water insoluble inorganic salts, which are less dense than the particle. Therefore, this particulate removed by decanting the supernatant until the particle was cleared.

Example 1: Preparation of Hydrogel Particles

Hydrogel particles were prepared according to Example 1 of WO 2004/071495 (high AMPS method). The process was terminated after the step in which the product was vacuum dried to remove residual solvents. Beads were then sieved to provide appropriate size ranges. Beads were either stored dry or in physiological saline and autoclaved. Unless otherwise stated, coupling was carried out on batches of microspheres having diameters between 70 and 185 μm unless otherwise stated. Coupling reactions were carried out on dried beads that were swollen in solvent prior to use.

Example 2: Synthesis of 4-Formylbenzyl-DO3A-tris(t-Bu Ester) (2)

The reaction is shown in Scheme 1. To a solution of DO3A-t-Bu-ester (5 g, 9.7 mmol) and 4-(Bromomethyl) benzaldehyde (1.93 g, 9.7 mmol) in anhydrous N,N-dimethylformamide (DMF) (60 mL) was added $K_2CO_3$ (1.6 g, 11.64 mmol). The reaction was stirred at room temperature for 4 hrs. The reaction progress was monitored by Rp-HPLC (FIG. 1). When completed, the reaction mixture was filtered and the solvent was removed. The product was purified by column chromatography (silica gel, MeOH: dichloromethane (DCM) from 0-10%) to give 2 (4.7 g, 76%) dull yellow powder. $^1$HNMR (CDCl$_3$, 300 MHz, 298K): δ 1.5 (27H, s, $^t$Bu), 2.2-2.9 (16H, m, CH$_2$), 3.0-3.1 (6H, bs, CH$_2$COOtBu), 3.2 (2H, s, CH$_2$), 7.7 (2H, d, J=8 Hz, Ph), 7.9 (2H, d, J=8 Hz, Ph), 10.0 (s, HCO); $^{13}$C NMR (CDCl$_3$, 75 MH, 298K): δ 27.6, 49.7, 55.4, 55.7, 59.1, 82.2, 82.6, 129.7, 130.8, 135.3, 144.4, 172.4, 173.2, 191.5. MS-ESI: m/z (%)=633.4 (100) [(M+H)$^+$], HRMS[(M+H)$^+$]=calcd. for: [C$_{34}$H$_{57}$N$_4$O$_7$]$^+$663.4220; found 663.4227.

Scheme 1.
Alkylation of 4-(bromomethyl)benzaldehyde into the DO3A-t-Bu-ester

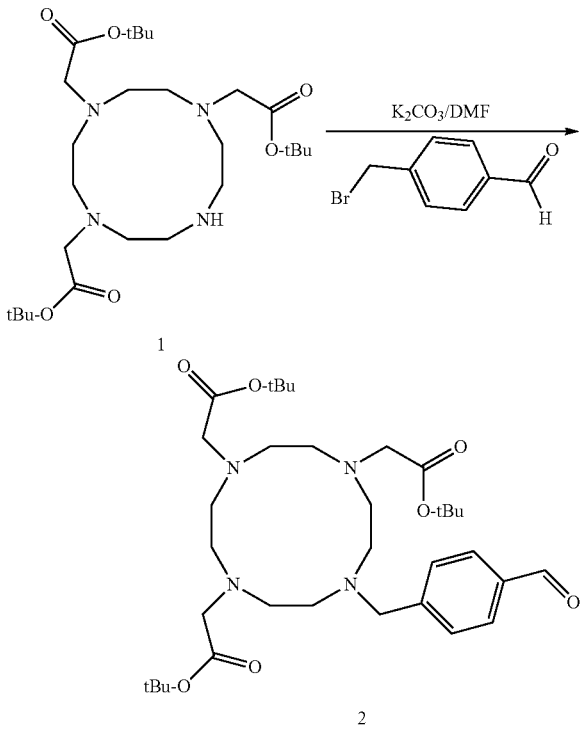

Example 3: Synthesis of DO3A-4-formylbenzyl (3)

Scheme 2 shows the deprotection of 4-formylbenzyl-DO3A-tris(t-Bu ester) (2) to provide DO3A-4-formylbenzyl (3). As shown in Scheme 1, Compound 2 (9.2 g, 14.6 mmol) was treated with HCl gas saturated with 1,4-dioxane (450 mL) and the mixture was then stirred at room temperature for 18 hr. Afterwards, ethyl ether (100 mL) was added and the solution was then kept in the refrigerator overnight. The precipitate was collected and washed with cold ethyl ether (200 mL). Finally, 8 g (qualitative yield) of dull white powder was obtained. $^1$HNMR (DMSO-d$_6$, 300 MHz, 298K): δ 2.9-3.4 (16H, m, CH$_2$), 3.6 (6H, s, CH$_2$), 4.3 (2H, s, CH$_2$), 7.8 (2H, d, J=8 Hz, Ph), 7.9 (2H, d, J=8 Hz, Ph), 10.0 (1H, s, HCO); $^{13}$C NMR (DMSO-d$_6$, 75 MHz, 298K): δ 48.7, 49.2, 50.0, 56.0, 66.4, 129.8, 131.9, 136.3, 170.7, 193.1. MS-ESI: m/z (%)=465.2 (100) [(M+H)⁺], HRMS [(M+1)⁺]: calcd. for: [C$_{22}$H$_{33}$N$_4$O$_7$]⁺465.2345; found 465.2349

Scheme 2. Deprotection

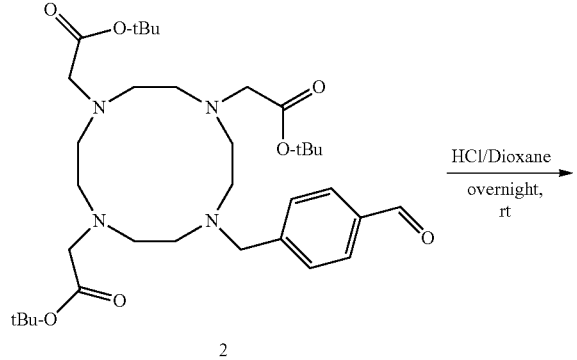

In an alternative procedure, deprotection is done with trifluoroacetic acid (TFA). Compound 2 was treated with neat trifluoroacetic acid (TFA) and the mixture was then stirred at room temperature for 3 hr. Afterwards, TFA removed and the resulting gummy solid was treated with ethyl ether and kept in the refrigerator overnight. The precipitate was collected and washed with cold ethyl ether.

Example 4: Acetylation of the Particle with 3

Scheme 3 shows Acetylation of the particles with DO3A-4-formylbenzyl (3).

Scheme 3. Acetalation of the particles with DO3A-4-formylbenzyl (3).

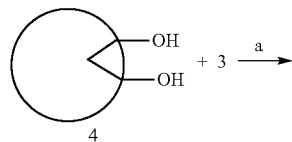

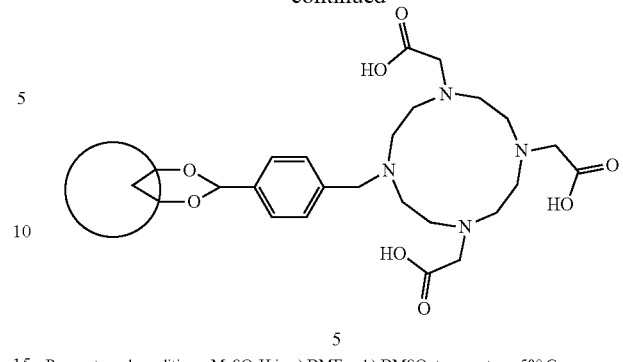

Figure 2:
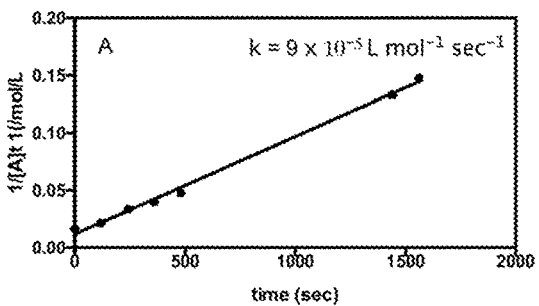
FIG. 2 shows the acetylation reaction of the particles with 3 in DMSO follows second-order reaction rate with rate constant $\kappa=2.4\times10^{-3}$ L mol$^{-1}$s$^{-1}$.
Figure 3:
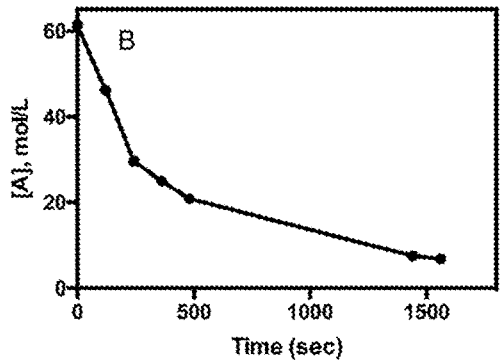
FIG. 3 shows the depletion of 3 over time acetylation reaction of the particles with 3 in DMSO.
Figure 4:
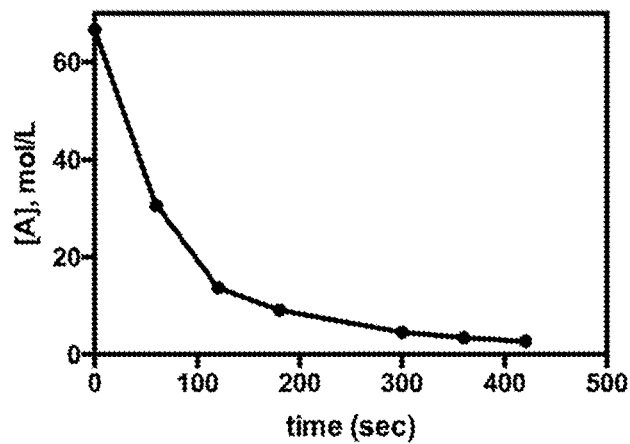
FIG. 4 shows the depletion of 3 over time in an acetylation reaction of the particles with 3 in DMF.

Reagents and conditions: MeSO₃H in a) DMF or b) DMSO, temperature, 50° C.

a) DMSO as the reaction solvent: 1 g of particles were swollen in 35 mL of anhydrous DMSO and 1 g of 3 (2.15 mmol) was added and mixed for 30 minutes to uniformly distribute the macrocycle compound (3) into the swollen particles. Then, 2.2 mL of methanesulfonic acid was added drop wise from a syringe through a 30 1/2 G needle and the reaction mixture was stirred at lower stirrer setting under N$_2$ at 50° C. for 26 hr. The progress of the reaction was monitored with HPLC (every two hours for the first eight hours and then at 24 and 26 hours) for the consumption of compound 3. The reaction mixture was filtered and the filtrate (5) was washed with DMSO (10 mL) followed by conspicuous amount of saturated sodium bicarbonate (to completely remove the acid) and followed by water. FIG. 2 shows that the reaction follows second order reaction rates, and FIG. 3 shows the depletion of 3 over time. The acetylated particles used for the subsequent reaction.

b) DMF as a reaction solvent: 929 mg (2.0 mmol) of 3 was dissolved in anhydrous DMF (30 mL) into which 1 g of particles was added and mixed for 30 minutes to uniformly distribute the macrocycle compound (3) into the particles. Then, 2.2 mL of methanesulfonic acid was added drop wise from a syringe through a 30 1/2 G needle and the reaction mixture was stirred at lower stirrer bar setting under N$_2$ at 50° C. for 8 hr. The progress of the reaction was monitored with HPLC every one hours for the consumption of compound 3. The reaction mixture was filtered and the filtrate (5) was washed with DMF (10 mL) followed by conspicuous amount of saturated sodium bicarbonate to completely remove the acid and followed by water. FIG. 4 shows the depletion of 3 over time. The acetylated particles used for the subsequent reaction.

Example 5: Chelation of Bismuth (6)

The acetylated particles (5) from the above reaction were resuspended in DI-water at a pH of 8-9, 1.94 mg of Bi(NO$_3$)$_3$·5H$_2$O or Bi(CF$_3$SO$_3$)$_3$ (4 mmol) was added and stirred at 80° C. for 1 hr. The final product gravity filtered and washed first with 0.1M acetic acid followed by water and an aqueous solution of sodium bicarbonate (0.1 M) and finally with a conspicuous amount of DI-water. The complete removal of bismuth salt was confirmed with an aqueous solution of potassium iodide (1%, w/v) as reported in the art. Note: Washing the bismuth particles with sodium bicarbonate may increase the swell-ability of the particles and neutralize acid residue formed.

Scheme 4. Chelation of bismuth to acetalated particles (5) to produce imageable bismuth particles.
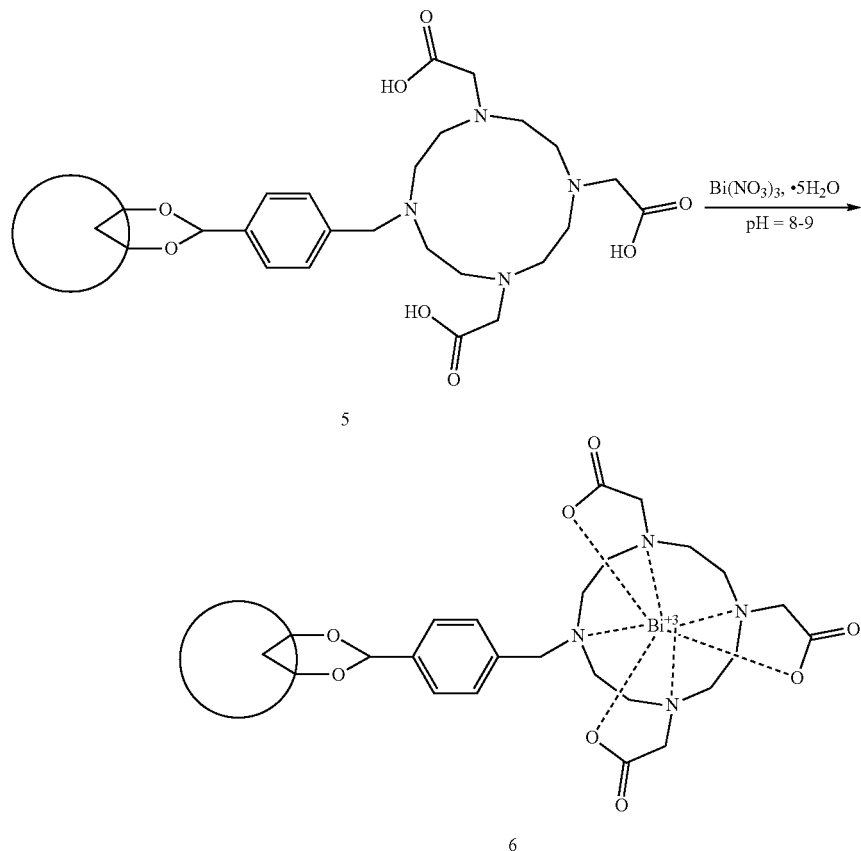
Example 6: Alternative Ligands for Bi Chelation: Synthetic Routes for DTTA-4-formylbenezyl (13) and DTPA-4-formylbenzylamide (15)
Scheme 5 provides synthetic routes for DTPA-4-formylbenezyl (13) and DTPA-4-formylbenzyl amide (15).

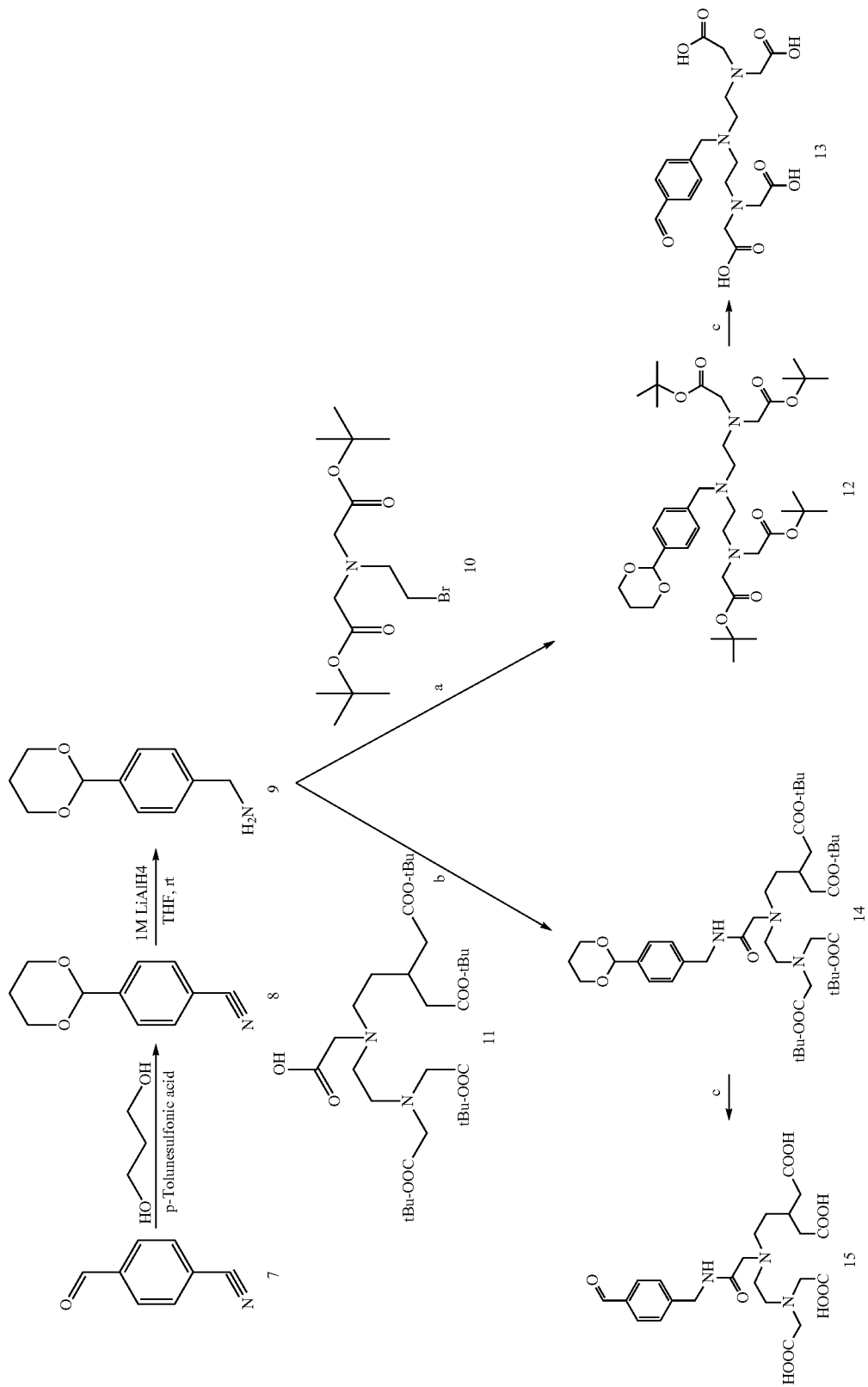

4-(1,3-dioxan-2-yl)benzonitrile (8)

The reaction was carried out as previously reported in the literature. Briefly, while a solution of compound 7 (2 g, 15.3 mmol) and propane-1,3-diol (4.65 g, 61.2 mmol) was stirred in toluene (100 mL), 4-methylbenzenesulfonic acid (0.26 g, 1.53 mmol) was added. The resulting mixture was refluxed for 6 h. Then, the mixture solution was washed with saturated sodium bicarbonate (100 mL×2), brine (100 mL×2) and dried over anhydrous $Na_2SO_4$. The solvent was evaporated under reduced pressure to give compound 8 as a white powder. MS: m/z (%)=190.1 (100) [(M+H)$^+$], HRMS [(M+H)$^+$]: calcd. for $[C_{11}H_{12}NO_2]^+$190.0871; found 190.0868.

4-(1,3-dioxan-2-yl)benzylamine (9)

The reaction was carried out as previously reported with slight modification. Briefly, to a solution of 100 mL $LiAlH_4$ (1M, 100 mmol) was added 4-(1,3-dioxan-2-yl)benzonitrile 8 (5 g) in anhydrous THF (70 mL) drop wise at ambient temperature. The reaction mixture was stirred for 2 hours. Then, water (3 mL), 10% aqueous NaOH (5 mL), and water 7 mL was added sequentially. The white slurry was diluted with THF (50 mL) and filtered. Removal of the solvent yielded 4-(1,3-dioxan-2-yl)benzylamine as a colorless oil, which was used in the subsequent reaction without further purification. MS-ESI: m/z (%)=194.1 (10) [(M+H)$^+$], 177.1 (100) [(M−NH$_3$)$^+$], HRMS [(M+H)$^+$]: calcd. for $[C_{11}H_{16}NO_2]^+$194.1179; found 194.1181.

Tetra-t-butyl-2,2',2'',2'''-((((4-(1,3-dioxane-2-yl)benzyl)azanediyl)bis(ethane-2,1-diyl)bis(azanetriyl)) tetraacetate (12)

To a solution of 9 (228 mg, 1.2 mmol) and N-(2-bromoethyl)-N-[2-1,1-dimethylethoxy)-2-oxoethyl]glycine 1,1-dimethylethyl ester (831.6 mg, 2.4 mmol) in anhydrous DMF (5 mL) was added $K_2CO_3$ (392 mg, 2.84 mmol). The reaction mixture was stirred at room temperature under nitrogen atmosphere for 24 hours. Then, the mixture was filtered and the solvent evaporated. The residue was dissolved in $CH_2Cl_2$ (20 ml) and the solution was washed with water (3×10 mL). The organic phase was dried ($Na_2SO_4$) and the solvent was removed by evaporation. The residual, yellowish viscous oil, was purified by column chromatography (silica gel, MeOH/DCM, 0:10) to give 530 mg (60%) of 12. MS-ESI: m/z (%)=465.3 (50), [(M−($C_{14}H_{25}NO_4$)$^+$], 736.4 (100) [(M+H)$^+$], HRMS[(M+H)$^+$]: calcd. for $[C_{39}H_{66}N_3O_{10}]^+$736.47; found 736.5.

DTTA-4-formylbenzylamide (2,2',2'',2'''-((((2-((4-formylbenzyl)amino)-2-oxoethyl)azanediyl)bis(ethane-2,1-diyl))bis(azanetriyl))tetraacetic acid) (13)

Compound 12 (520 mg, 0.7 mmol) was treated with HCl gas saturated 1,4-dioxane (100 mL) and the mixture was then stirred at room temperature overnight. Afterwards, ethyl ether (100 mL) was added and the solution was then kept in the fridge overnight. The precipitate was collected and washed with cold ethyl ether (100 mL). Finally, 340 mg of dull yellow powder was obtained and used for subsequent reaction.

Tetra-t-butyl-2-, 2',2'',2'''-((((2-((4-(1,3-dioxan-2-yl)benzyl)amino)-2-oxoethyl)azanediyl)bis(ethane-2,1-diyl))bis(azanetriyl))tetraacetate (14)

To a solution of DTPA-tetra, t-butyl ester (1.0 g, 1.62 mmol) and 9 (313 mg, 1.62 mmol) in anhydrous DMF (15 mL) at 0 C, EDC·HCl (473 mg, 2.5 mmol) was added followed by DMAP (473 mg, 2.5 mmol. The resulting reaction mixture was stirred at room temperature overnight. DMF removed and the residue dissolved in DCM and washed with water to remove excess EDC·HCl and urea by-product. The organic phase was dried over sodium sulphate, filtered and the solvent was evaporated to obtain the crude product, which was purified by column chromatography (MeOH/DCM, 0:10) to give a yellowish oil residue, 852 mg (66%) of 14. It was used for subsequent reaction.

DTPA-4-formylbenzylamide (2,2',2'',2'''-((((2-((4-formylbenzyl)amino)-2-oxoethyl)azanediyl)bis(ethane-2,1-diyl))bis(azanetriyl))tetraacetic acid) (15)

Compound 14 (850 mg, 0.8 mmol) was treated with HCl gas saturated as described previously. 548 mg of dull yellow powder was obtained. MS-ESI: m/z (%)=533.2 (20) [(M+Na)$^+$], 511.1 (100) [(M+H)$^+$], HRMS [(H+1)$^+$]: calcd. for $[C_{22}H_{31}N_4O_{10}]^+$511.5; found 511.2.

Example 7: General Procedure for Bismuth Chelation to Linear and Macrocycle Ligands Ligand (3, 13 or 15) was dissolved in DI water and the pH adjusted to 8-9 with 1N NaOH. To this solution, 1.5 mole equivalent of $Bi(NO_3)_3.5H_2O$ or $Bi(CF_3SO_3)_3$ was added and stirred at 80° C. for 1 hrs. The mixture was cooled to room temperature and the pH adjusted to 7.0 with 1N NaOH. The final product (16, 17 or 18) was obtained after the insoluble salts were centrifuged and supernatant was passed through Chelex 100 and lyophilized.

Compound 16: MS-ESI: m/z (%)=693.2 (10) [(M+Na)$^+$], 671.2 (100) [(M+H)$^+$], 465.2 (40) [(M-Bi)$^+$], HRMS[(M+H)$^+$]: calcd. for $[C_{22}H_{30}N_4O_7Bi]^+$671.1911; found 671.1918.

Compound 17: MS-ESI: m/z (%)=682.1 (25) [(M+Na)$^+$], 660.1 (100) [(M+H)$^+$], HRMS[(M+H)$^+$]: calcd. for $[C_{20}H_{25}N_3O_9Bi]^+$660.1393; found 660.1395.

Compound 18: MS-ESI: m/z (%)=739.1 (10) [(M+Na)$^+$], 717.1 (100) [(M+H)$^+$], HRMS [(M+H)$^+$]: calcd. for $[C_{22}H_{28}N_4O_{10}Bi]^+$717.1599; found 717.1609.

Figure 5:
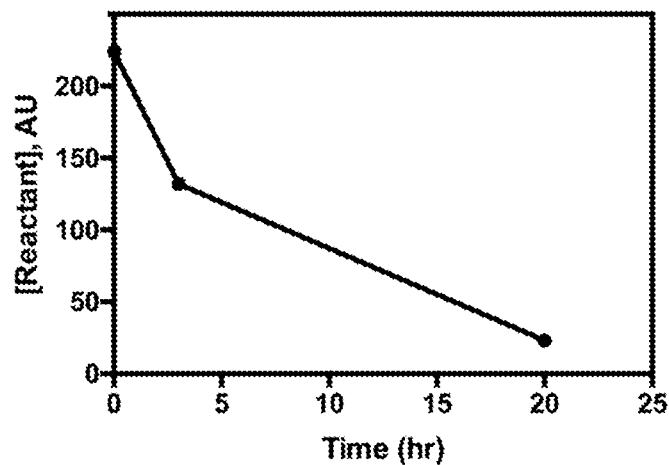
FIG. 5 shows the depletion of 17 over time in an acetylation reaction of the particles with 17.

Compound 20: Method for the Acetylation of 6 was followed but the product was not visible under CT. Acetylation was confirmed by monitoring the consumption of 17 by HPLC. (FIG. 5) Assuming the bismuth was de-chelated from the ligand (and compound 19 is formed instead, Scheme 7), due to the acidic condition of the reaction mixture, the content of the vial was filtered and washed. The washed, ligand activated particles were chelated with bismuth following similar procedure for bismuth chelation to obtain compound 20.

Figure 6:
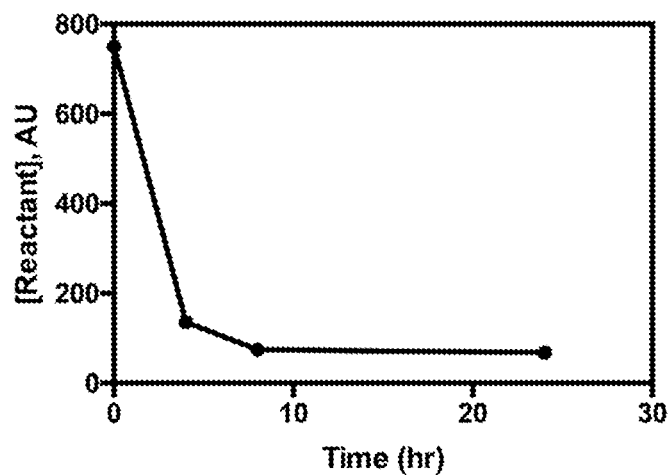
FIG. 6 shows the depletion of 18 over time in an acetylation reaction of the particles with 18.

Compound 22: Method for the Acetylation of 6 was followed but the product was not visible under CT. Acetylation was confirmed by monitoring the consumption of 18 by HPLC. (FIG. 6) Assuming the bismuth was de-chelated from the ligand (and compound 21 is formed instead, Scheme 7), due to the acidic condition of the reaction mixture, the content of the vial was filtered and washed. The washed, ligand activated particles were chelated with bismuth following similar procedure for bismuth chelation to obtain compound 22.

Scheme 6 shows the chelation of ligands a) $Bi(NO_3)_3.5H_2O$ or $Bi(OSO_2CF_3)_3$.

Scheme 6. Chelation of ligands
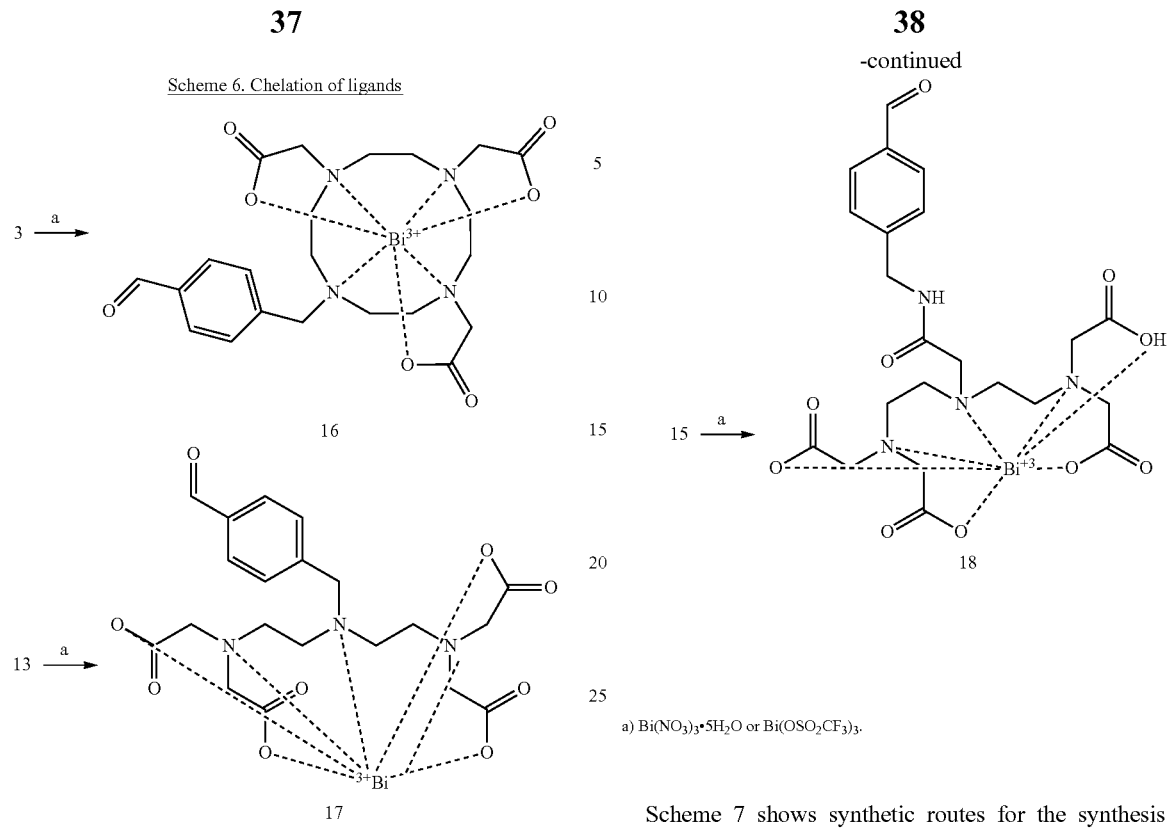
a) Bi(NO$_3$)$_3$·5H$_2$O or Bi(OSO$_2$CF$_3$)$_3$.
Scheme 7 shows synthetic routes for the synthesis of bismuth chelated particles.

Scheme 7.
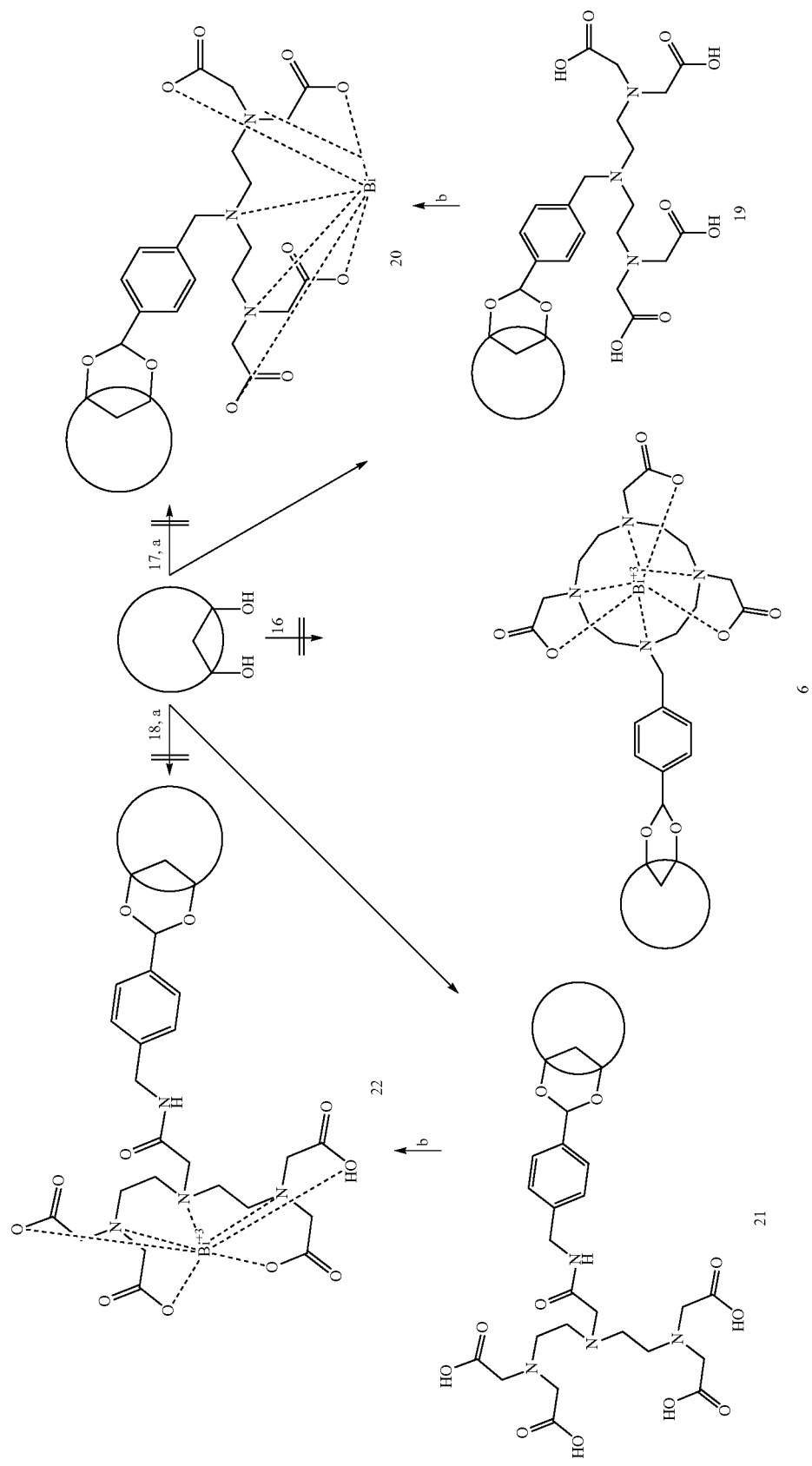
Reagents and conditions: a) MeSO₃H, DMF, 7 hrs, 50° C.; b Bi(NO₃)₃·5H₂O or Bi(OSO₂CF₃)₃, pH 8-9, 1 hr, 80° C.

Example 8: Alternative Synthetic Route

Scheme 8 is a route for the synthesis of novel reactive macrocycle. Reagents and conditions: SOCl$_2$, DCM, rt; 2 h, reflux; cooled, H$_2$O, 15 min, cooled; 1 h, rt; on, 4-DMPA, EtN=C=N(CH$_2$)$_3$NMe$_2$·HCl, DMF, 45 min, 0° C.' THF, 0° C. rt; overnight, rt.

Scheme 8. Synthetic routes for the synthesis of novel reactive macrocycle.

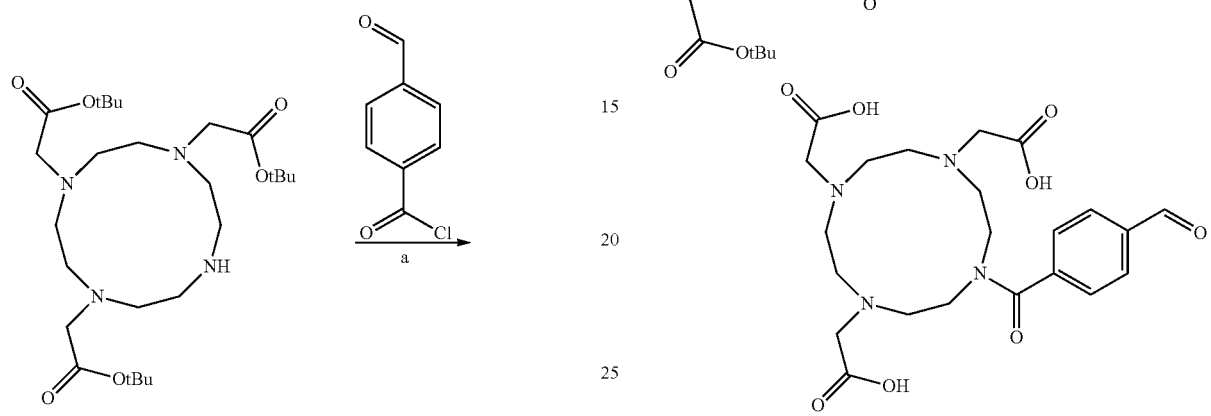

Example 9: Characterization of Bismuth Particle 6 from Scheme 4 (Example 5)

Figure 7:
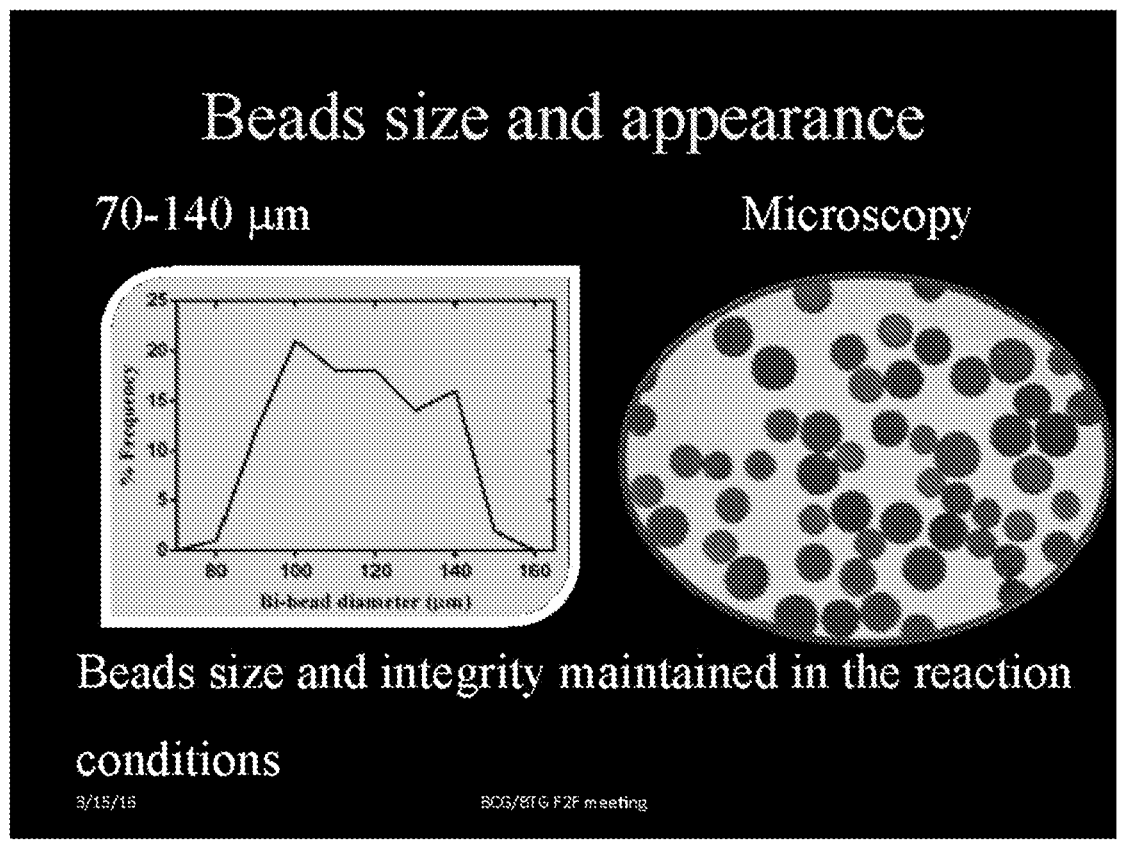
FIG. 7 shows the bismuth particle size and a microscopy image of the beads.
Figure 8:
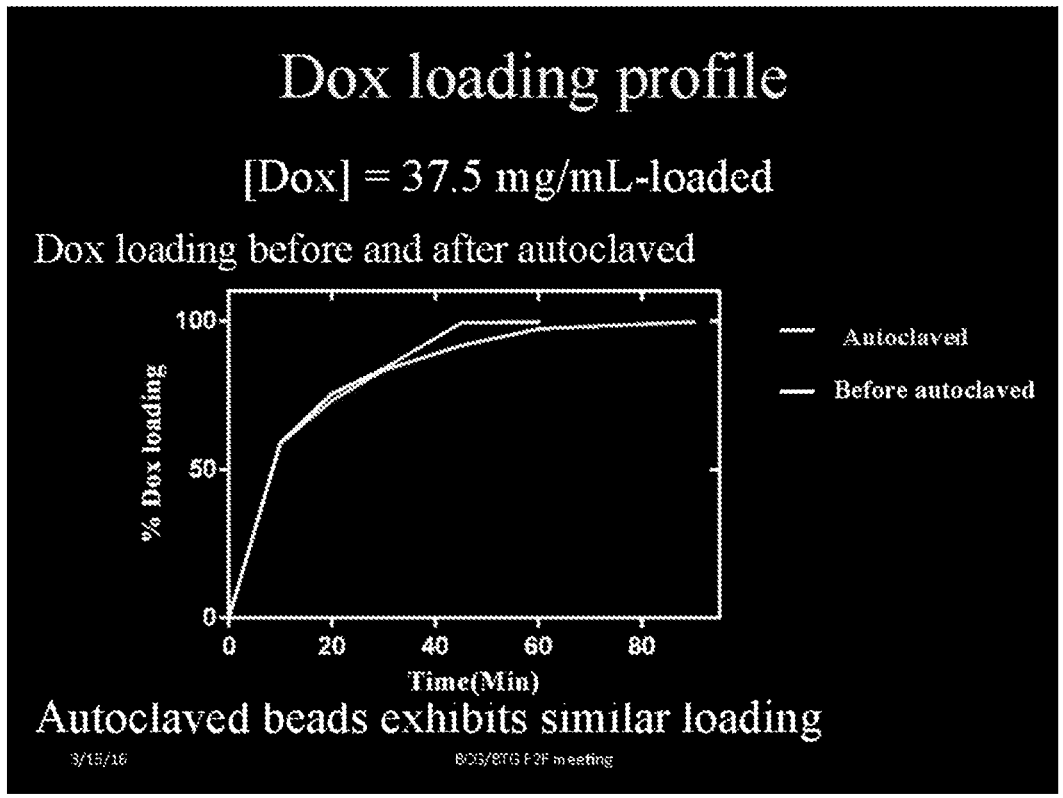
FIG. 8 shows the effect of doxorubicin loading before and after autoclaving the bismuth particles.
Figure 9:
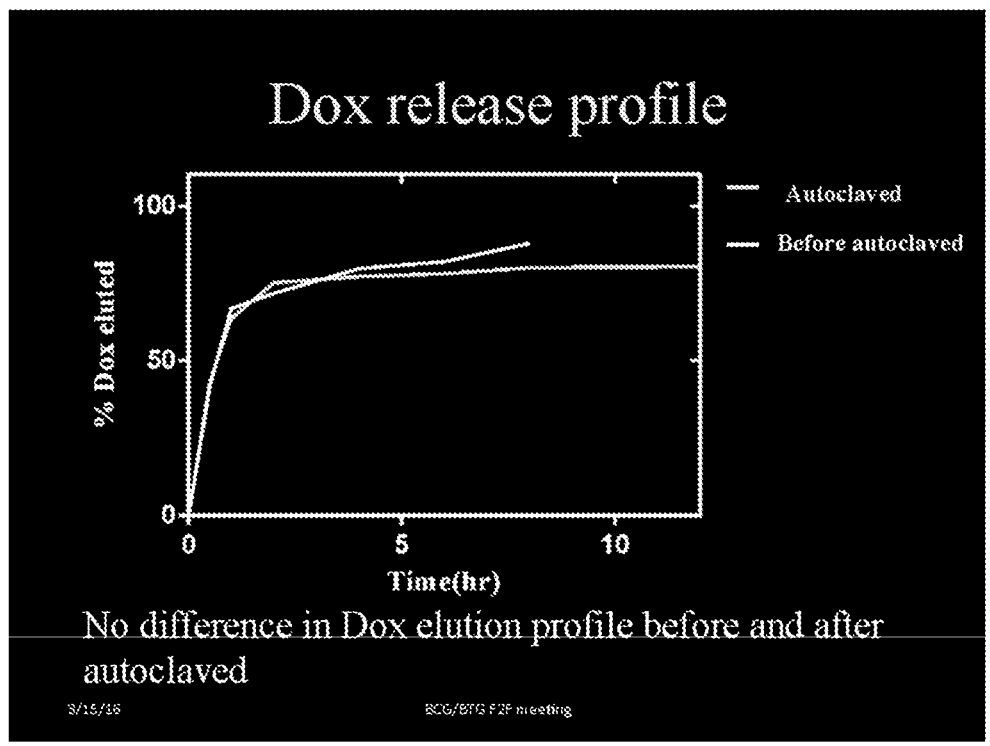
FIG. 9 shows release of doxorubicin from the beads before and after autoclaving the bismuth particles.
Figure 10:
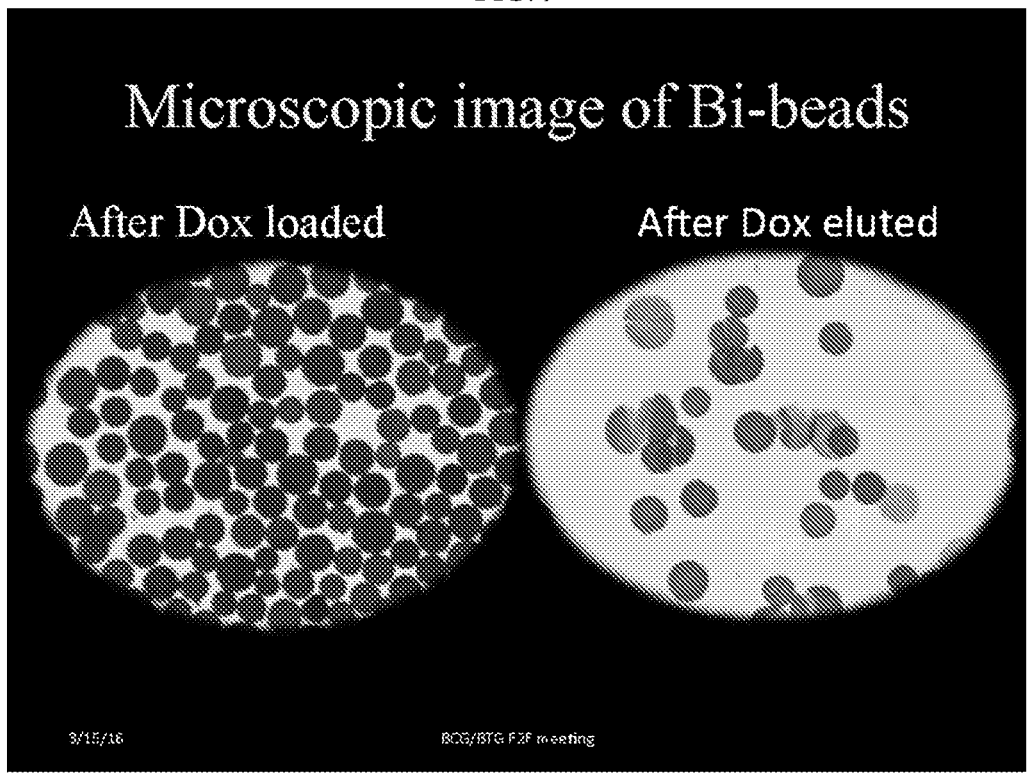
FIG. 10 shows microscopic images of the bismuth particles before and after doxorubicin elution.
Figure 11:
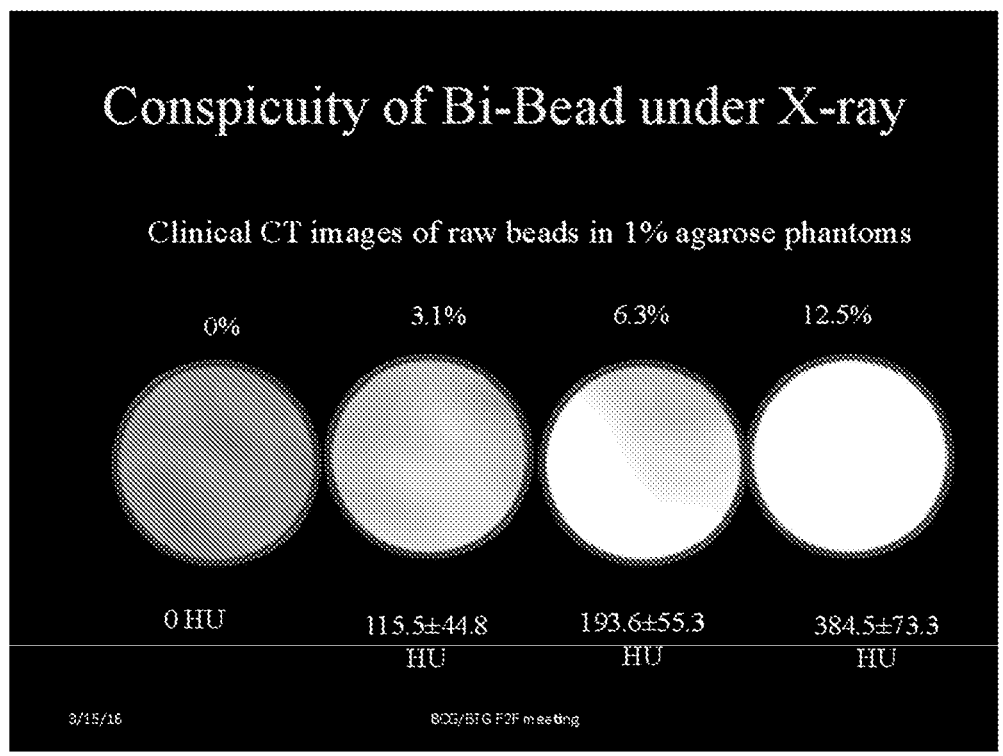
FIGS. 11-12 show the conspicuity of the bismuth particles under X-ray.
Figure 12:
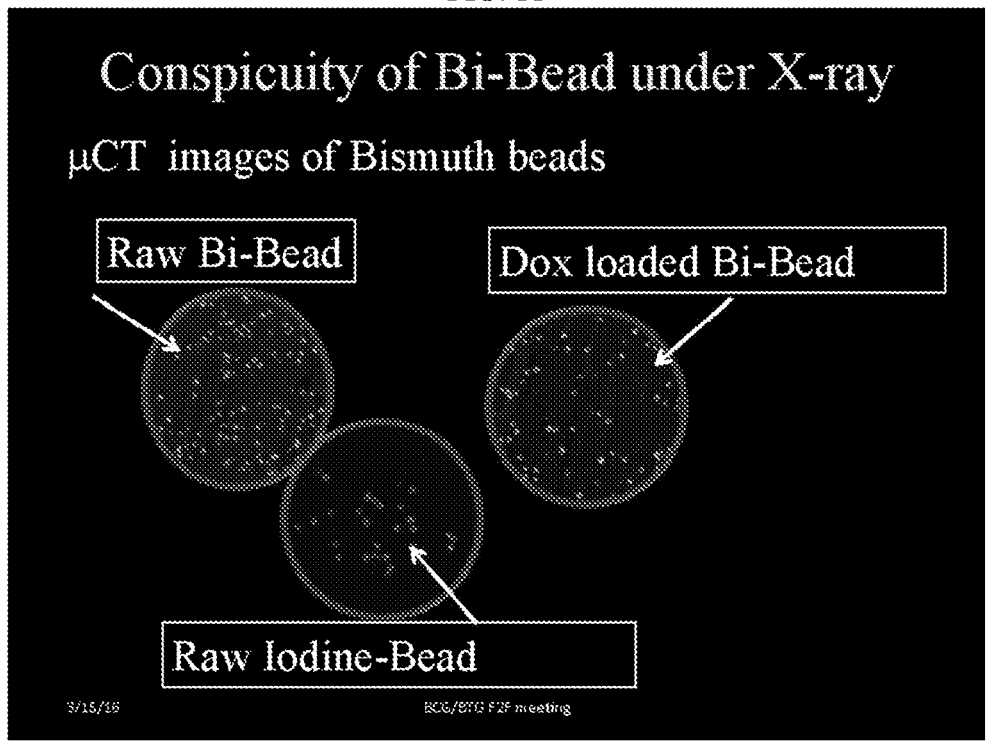

As shown in FIG. 7, the bismuth particle size and integrity were maintained during the reaction conditions. In data not shown and in FIG. 8, autoclaving made the bismuth particles look whiter, but had no effect on the drug loading ability (doxorubicin) of the bismuth particles. As shown in FIG. 9, there was no effect on doxorubicin elution before and after autoclaving the bismuth particles. FIG. 10 shows microscopic images of the bismuth particles before and after doxorubicin elution. FIGS. 11-12 show the conspicuity of the bismuth particles under X-ray.

Example 10: Synthesis of Second Generation Bismuth Particles

Second generation bismuth particles were synthesized according to Scheme 9.

Scheme 9: Synthesis of second generation bismuth particles

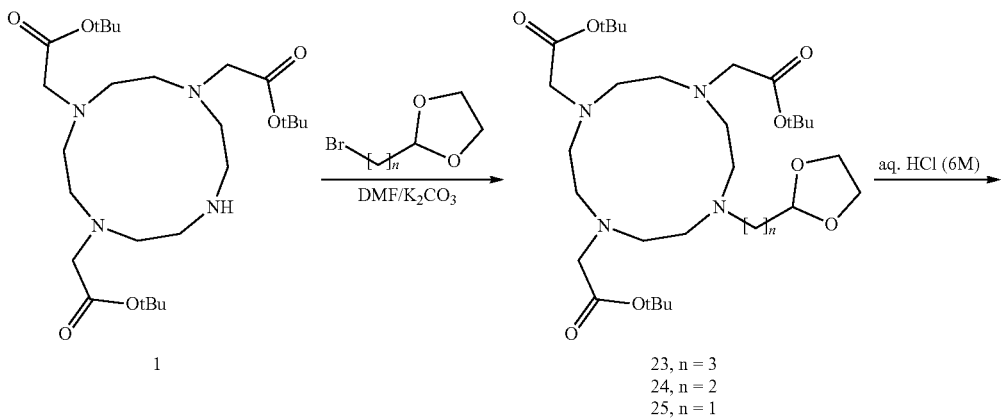

23, n = 3
24, n = 2
25, n = 1

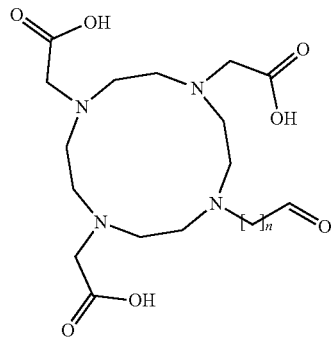

26, n = 3
27, n = 2
28, n = 1

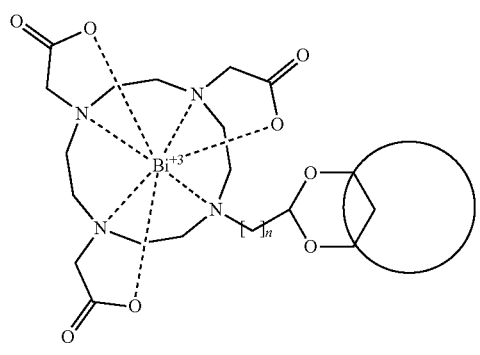

32, n = 3
33, n = 2
34, n = 1

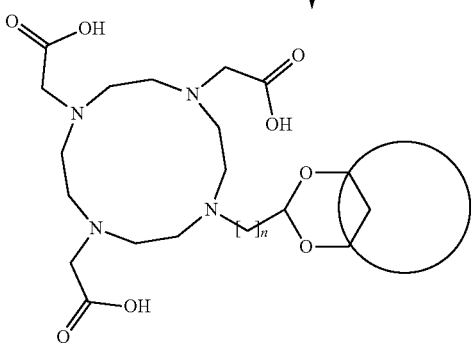

29, n = 3
30, n = 2
31, n = 1

1,3-dioxolan-2-yl) propyl-DO3A-tert-Bu Ester (23)

To a solution of 2-(3-bromopropyl)-1,3-dioxolane (3.4 mmol, 0.480 mL) and DO3A-t-Bu-ester (2.9 mmol, 1.5 g) in anhydrous N,N-dimethylformamide (DMF) (12 mL, to give 0.24M nucleophile solution) was added $K_2CO_3$ (3.62 mmol, 500 mg). The reaction mixture was allowed to stir at room temperature for 24 hrs (the progress of the reaction was monitored by mass spectrometer). The solvent was removed and the crude product was dissolved in acetonitrile and precipitated from ethyl ether, filtered and ethyl ether removed from the filtrate by evaporation to give the titled compound and used for the next reaction without further purification. ESI-MS (m/z) calcd. for: $[C_{32}H_{60}N_4O_8+H]^+$ 629.9; found 629.4.

1,3-dioxolan-2-yl)ethyl-DO3A-tert-Bu Ester (24)

The synthetic method used for synthesis 23 was followed. ESI-MS (m/z) calcd. for: $[C_{31}H_{58}N_4O_8+H]^+$ 615.8; found 615.4

1,3-dioxolan-2-yl)methyl-DO3A-tert-Bu Ester (25)

To a solution of 2-(bromomethyl)-1,3-dioxolane (3.4 mmol, 0.363 mL) and DO3A-t-Bu-ester (2.9 mmol, 1.5 g) in anhydrous N,N-dimethylformamide (DMF) (12 mL, to give 0.24M nucleophile solution) was added $K_2CO_3$ (3.62 mmol, 500 mg). The reaction was allowed to stir at 50° C. for 4 days in the dark (the progress of the reaction was monitored by MS). The solvent was removed and the crude product was dissolved in acetonitrile and precipitated from ethyl ether, filtered and ethyl ether removed to provide product and used as is for the next reaction. ESI-MS (m/z) calcd. for: $[C_{30}H_{57}N_4O_8+H]^+$601.8; found 601.4.

4-butanal-DO3A (26)

1,3-dioxolan-2-yl)propyl-DO3A-tert-Bu ester (23) suspended in aq. HCl (6 M, 10 mL) overnight. The consumption of the starting material was monitored by mass spectrometer. tBuOH and the glycol were extracted with chloroform and the product was lyophilized from the aqueous solution and used for the next reaction without further purification. ESI-MS (m/z) calcd. for: $[C_{18}H_{32}N_4O_7+H]^+$417.48; found 417.2.

3-Propanal-DO3A (27)

Synthetic method used for synthesis 26 was followed. ESI-MS (m/z) calcd. for: $[C_{17}H_{30}N_4O_7+H]^+$403.4; found 403.2

3-Ethanal-DO3A (28)

Synthetic method used for synthesis 26 was followed. ESI-MS (m/z) calcd. for: $[C_{16}H_{28}N_4O_7+H]^+$389.4; found 389.2.

Acetylated Particles (29, 30 and 31)

1000 mg of particles were swollen in 30 mL of anhydrous DMF and 4-Butanal-DO3A (26) or 4-propanal or 3-propanal-DO3A (27) or 3-ethanal-DO3A (28) (1.2 g) was added and stirred till all the aldehyde get dissolved. Finally 2.2 mL of methanesulfonic acid was added drop wise (1 mL syringe and 30G1/2 needle). The reaction was stirred under N2 at 50° C. for 22 hrs. The product was washed with DMF (5×30 mL) and with water. The acid was neutralized with 0.1M NaHCO₃ (4×10 mL) and rinsed with water. The obtained acetylated particles were used for the next reaction.

2$^{nd}$ Generation Bismuth Particles (32, 33, or 34)

Acetylated particles (29, 30 or 31) suspended in basic-water at a pH of 8.0 (using 1:1 mixture of 0.1M NaHCO₃ and water, 25 mL), 3281 mg of bismuth (III) trifluoromethanesulfonate, (Bi(CF₃SO₃)₃, 5 mmol) added and stirred at 70-80° C. for 60 minutes. The final product was filtered through a fritted syringe filter under gravity and thoroughly washed with 0.3M acetic acid (1 L) followed by water (until there is no Bi$^{+3}$ is observed, which was monitored with KI solution as described in the prior art), washing was continued with sodium bicarbonate (0.05M, increment of particle volume was observed), water (pH=5) and NaCl solution (0.9 M, reduction of particle volume was observed) in which the particles were stored until final use.

Example 10: Radiopacity of Second Generation Bismuth Particles

Figure 13:
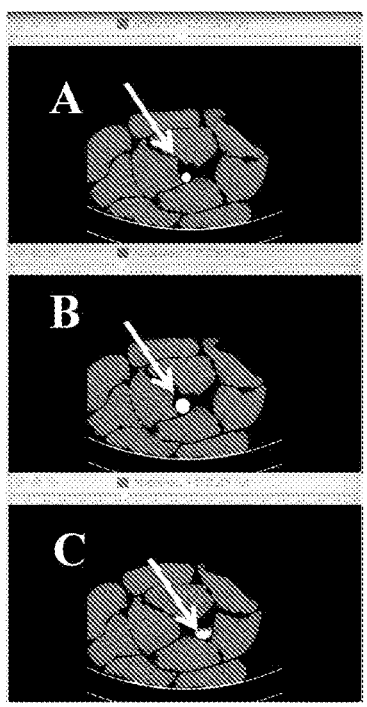
FIG. 13 shows representative example of radiopacity for bismuth microspheres 10a (A), 11a (B) and 12a (C) at 80 kV. The arrow indicates the microsphere.

The resulting bismuth particles were scanned with a prototype whole-body photon-counting CT scanner (Siemens Healthcare). The particles were suspended in saline (0.9% NaCl solution) and imaged with CT scanner to determine their attenuation with the following settings: 210 mAs, at 80, 100 and 120 kV, 1-mm×1-mm thickness. The results are given in the Table and representative scans are shown in FIG. 13.

| Bismuth particles | Radiopacity (HU) Energy KV | | |
|---|---|---|---|
| | 80 | 100 | 120 |
| 32 | 849 ± 27 | 732 ± 19 | 777 ± 17 |
| 33 | 907 ± 57 | 802 ± 42 | 865 ± 30 |
| 34 | 518 ± 45 | 437 ± 33 | 456 ± 36 |

Example 11: Bismuth Chelation Using Solvent Method

Coupling of the Macrocycle:

To a pre-dried reactor was added anhydrous NMP (N-methylpyrrolidinone) 25 mL as a reaction solvent. 3000 mg of dried macrocycle prepared according to Example 3 (4-formylbenzyl DO3A-(3)), was added, and rinsed in the reactor with anhydrous NMP (5 mL). Then, 2.2 mL of methanesulfonic acid was added to the reactor and the reactor was warmed to a 55° C. internal temperature. To the reactor was added 1 g of particles (prepared according to Example 1, size 105-185 μm) and the reaction mixture was stirred at lowest stirrer bar setting under N₂ at 55° C. for 24 hrs. The progress of the reaction was monitored with HPLC for the consumption of the macrocycle with detection at 256 nm. The reaction mixture liquid phase was then removed and the filtrate was washed with NMP×5 (150 mL). The filtrate was then suspended in water and neutralized with 0.1M sodium carbonate to pH 9, followed by washing with water (150 mL) and NMP (250 mL) and aspiration of the solvent. The derivatized particles were used directly in the subsequent reaction.

Chelation of the Bismuth:

Fresh anhydrous NMP (30 mL) was charged to the reactor under N₂. To this was added pyridine (2 eq relative to bismuth triflate), and the reactor contents were then warmed to 55° C. 1.5 eq Bismuth triflate (eq determined from HPLC analysis data from the previous stage) was then rinsed in with 5 mL of anhydrous NMP. The resulting suspension was stirred at 55° C. under N₂ overnight. The reaction mixture liquid phase was removed and the filtrate was washed with NMP (150 mL). The filtrate was then suspended in 0.9% saline and then washed with 0.9% saline (250 mL) followed by aspiration of the saline. The resulting off white beads were transferred to a Schott vial, using additional saline, autoclaved at 121° C. for 30 mins and then cooled to room temperature.

Example 12: Further Coupling Example

Synthesis of tri-tert-butyl 2,2',2"-(10-(4-formyl-2-nitrophenyl)-1,4,7,10-tetraazacyclododecane-1,4,7-triyl)triacetate Scheme 10

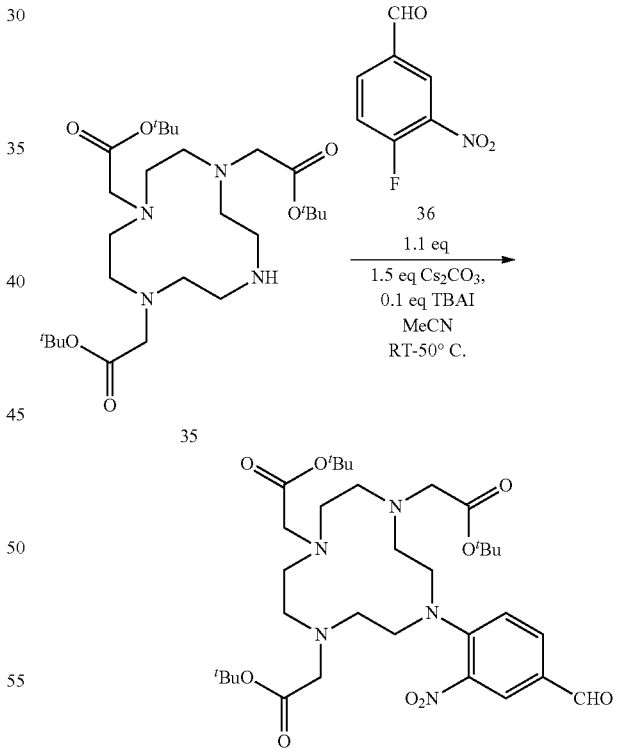

To a pre-dried, 2 necked 500 mL round-bottomed flask containing a stirrer bar, under a nitrogen atmosphere were added DO3A-tri-tert-butyl ester (35) (20.00 g, 1.0 eq), 4-fluoro-3-nitrobenzaldehyde (36) (7.29 g, 1.1 eq), cesium carbonate (18.99 g, 1.5 eq) and tetrabutyl ammonium iodide (1.44 g, 0.1 eq). To this mixture was added 200 mL of dry MeCN and the reaction mixture was stirred at room temperature for 3 h followed by heating at 50° C. for a further 1 h 40 mins. The reaction was followed by HPLC and TLC. At the completion of the reaction, identified by consumption of the DO3A-tri-tert-butyl ester, the reaction mixture was cooled to RT, and transferred to a 1 L separating funnel, diluting with EtOAc (500 mL). The bright orange solution was washed with DI water (4×100 mL), dried with magnesium sulfate, filtered and concentrated to dryness to give a thick orange syrup which was purified by column chromatography and dried under high vacuum to give the title product as a thick orange syrup (20.79 g, 80.59% yield). 1H NMR: (400 MHz, CDCl3) δ ppm: 9.76 (s, 1H), 8.11 (d, J=2H, 1H), 7.80 (q, J1=8.9 Hz, J2=2 Hz, 1H), 7.15 (d, J=9 Hz, 1H), 3.63 (t, J=5.8 Hz, 4H), 3.34 (s, 2H), 3.24 (s, 4H), 3.03 (t, J=5.8 Hz, 4H), 2.79 (m, 4H), 2.73 (m, 4H), 1.46 (s, 9H) 1.44 (s, 18H). 13C NMR: (100 MHz CDCl$_3$) δ ppm: 188.6, 170.9, 170.6, 148.4, 132(+), 130.7(+), 125.1, 118.7, 81.1, 57.5(−), 52.8(−), 52.2(−), 52(−), 51(−), 28.2.

Synthesis of 2,2′,2″-(10-(4-formyl-2-nitrophenyl)-1, 4,7,10-tetraaza cyclo dodecane-1,4,7-triyl)triacetic Acid tetrahydrochloric Acid (Macrocycle 38)

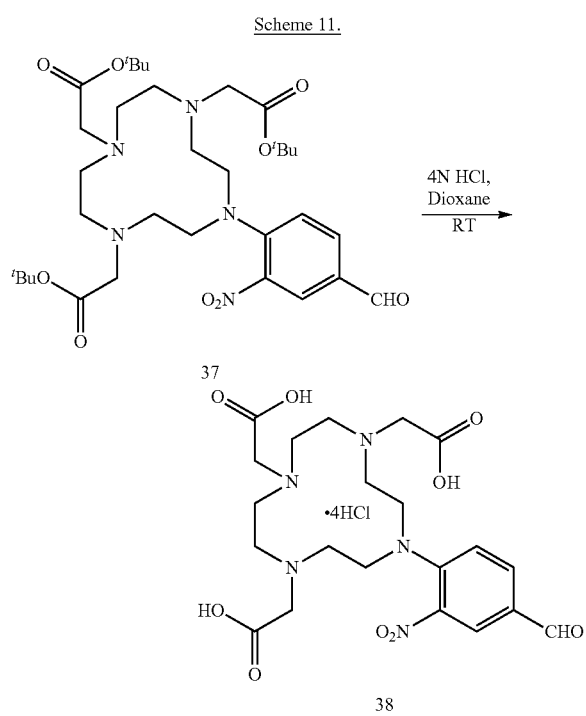

To a 1 neck 1 L flask containing tri-tert-butyl 2,2′,2″-(10-(4-formyl-2-nitrophenyl)-1,4,7,10-tetraazacyclododecane-1,4,7-triyl)triacetate (19.05 g, 1.0 eq) under a nitrogen atmosphere was added a large stirrer bar and 40 mL of anhydrous DCM. The thick oil was stirred until a solution was obtained. To this stirring solution was added 4N HCl in dioxane (360 mL, 50 eq). The resulting yellow was left to stir for 65 h, whereby a three phase mixture was obtained consisting of a pale yellow solution, a fine yellow precipitate and a thick insoluble brown/yellow syrup. HPLC analysis of the three phases showed that the syrup and precipitate were primarily consisted of the desired product. To this suspension was added 500 mL of diethyl ether and the mixture cooled under refrigeration for 4 days. During this time, the syrup solidified. The resulting suspension was dispersed and, due to the hygroscopic nature of the material, rapidly filtered in a large Büchner funnel, washed with diethyl ether and transferred to a vacuum oven. The material was dried under high vacuum to give an amorphous hygroscopic yellow solid (18.93 g, 97% yield) which was used without further purification.

Synthesis of Bismuth Containing Microparticles

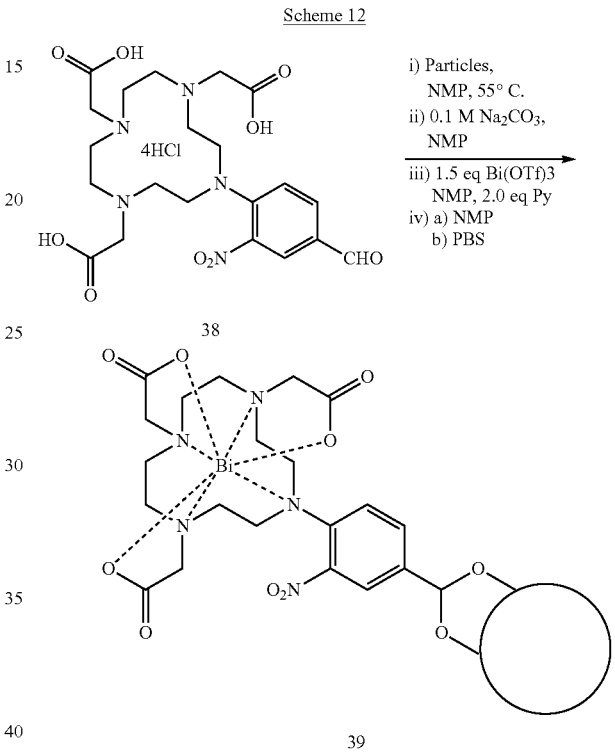

To a pre-dried reactor was added anhydrous NMP (N-methylpyrrolidinone) 20 mL as a reaction solvent. 2000 mg of macrocycle 38 (of scheme 11) was added, rinsed in with anhydrous NMP (10 mL). Then 1 g of particles (beads) prepared according to Example 1 were added, rinsed into the reactor with a further 5 mL of NMP and the reaction mixture was stirred at a lower stirrer bar setting under N$_2$ at 55-56° C. for up to 65 hr. The progress of the reaction was monitored with HPLC for the consumption of the macrocycle A (256 μm). The reaction mixture liquid phase was removed and the filtrate was washed with NMP (90 mL). The filtrate was then suspended in water and neutralized with 0.1M sodium carbonate to pH 9. The filtrate was then washed with water (90 mL) and NMP (250 mL) followed by aspiration of the solvent. The acetylated particles were used directly in the subsequent reaction. Fresh anhydrous NMP (30 mL) was charged to the reactor under N$_2$. To this mixture was added pyridine (0.54 mL, 2 eq relative to Bi(OTf)$_3$), the reactor contents warmed to 55° C., then bismuth triflate (2.486 g, 1.5 eq-required quantities determined from HPLC analysis data from previous stage), rinsed in with 5 mL of anhydrous NMP. The resulting suspension was stirred at 55° C. under N$_2$ overnight. The reaction mixture liquid phase was removed and the filtrate was washed with NMP (250 mL). The filtrate was then suspended in phosphate buffered saline (PBS), neutralized to pH 7 with 0.1M $Na_2CO_3$ and then washed with PBS (250 mL) and followed by aspiration of the solvent. The resulting mustard yellow particles were transferred to a 50 mL Schott vial in fresh PBS, and autoclaved at 121° C. for 30 mins, then cooled to room temperature.

Example 13: Coupling of Bismuth Subsalicylate

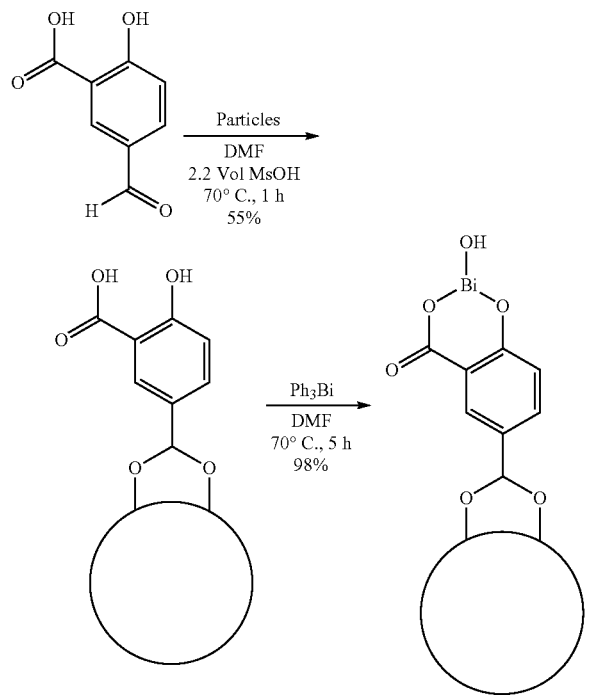

Scheme 13

In this example, the particles used were prepared according to Example 1, but were of the "Low AMPS" version of Example 1 of WO 2004/071495. The particles used were of the size range 355-500 µm.

Coupling bismuth subsalicylate to the particles lead to significant expansion of the particles during autoclaving. In this example, the particles were subjected to additional crosslinking with terephthalaldehyde prior to use in order to reduce swelling during autoclaving.

Preparation of Particles

Dried microspheres prepared according to Example 1 of the Low AMPS formulation (1.000 g) were resuspended in anhydrous DMF (60 mL) with gentle stirring. 20 mg of Terephthalaldehyde was added and the reaction was initiated by the addition of 2.2 mL of Methanesulphonic acid. The reaction proceeded under a nitrogen blanket for 24 hrs at 70° C. The resulting crosslinked microspheres were used without purification and directly for the following stage.

5-Fluorosalicylic Acid (5-FSA) Coupling

To the microspheres from the previous stage, suspended in anhydrous DMF and methanesulphonic acid, was added 1.678 g of 5-FSA. The reaction proceeded for 24 hrs at 70° C. with constant gentle stirring under a nitrogen blanket. Excess reactants were then removed by aspiration of the reaction mixture from the microspheres followed by 5 washes with hydrous DMF at 70° C. for 15 minutes each cycle.

Chelation of Bismuth.

To the terephthalaldehyde crosslinked, salicylate coupled microspheres from the previous reaction was added 2.45 g of triphenyl bismuthine in DMF (60 mL). The reaction proceeded at 70° C. for 24 hr under a nitrogen blanket. The bismuth microspheres were then gradually transferred to 0.9% saline by successive washes with 0.3M acetic acid solution (60 mL) and then 0.9% Saline (5 washes of 100 mL), each extraction cycle was performed at 70° C. for 15 minutes.

Bulk microspheres were dispensed into 20 mL Schott FIOLAX® clear glass vials containing 2 mL of microspheres in 5 mL saline packing solution, and sealed with bromobutyl Fluro Tec® injection stoppers and FOTO caps, followed by autoclaving at 121° C. for 30 min.

Example 14: Characterization of Radiopaque Beads

The dry weight of beads was measured by removing the packing saline and wicking away remaining saline with a tissue. The beads were then vacuum dried at 50° C. overnight to remove water, and the dry bead weight and solid content (w/w %) of polymer were obtained.

The bismuth content (w/w %) in dry beads were measured by inductively coupled plasma optical emission spectroscopy (ICP-OES) against a bismuth standard. For the bismuth content in wet beads, the calculation is:

Bead solid content (%)×bismuth content in dry beads (%). An alternative way to express the bismuth content is mg Bi/mL wet Example 15—Further X-Ray Analysis of Individual Radiopaque Beads Micro-CT was used to evaluate the radiopacity of samples of radiopaque embolic beads prepared according to Examples 10, 11 and 13. The samples were prepared in Nunc® cryotube vials (Sigma-Aldrich product code V7634, 48 mm×12.5 mm). The beads were suspended in 0.5% agarose gel (prepared with Sigma-Aldrich product code A9539). The resulting suspension is generally referred to as a "bead phantom". To prepare these bead phantoms, a solution of agarose (1%) is first raised to a temperature of approximately 50° C. A known amount of the beads is then added, and the two gently mixed together until the solution starts to solidify or gel. As the solution cools it gels and the beads remain evenly dispersed and suspended within the agarose gel.

Bead phantoms were tested for radiopacity using micro-Computer Tomography (Micro-CT) using a Bruker Skyscan 1172 Micro-CT scanner at the RSSL Laboratories, Reading, Berkshire, UK, fitted with a tungsten anode. Each phantom was analyzed using the same instrument configuration with a tungsten anode operating at a voltage of 64 Kv and a current of 155 µA. An aluminium filter (500 µm) was used.

Acquisition Parameters:
Software: SkyScan 1172 Version 1.5 (build 14)
NRecon version 1.6.9.6
CT Analyser version 1.13.1.1
Source Type: 10 Mp Hamamatsu 100/250
Camera Resolution (pixel): 4000×2096
Camera Binning: 1×1
Source Voltage kV: 65

Source Current uA: 153
Image Pixel Size (um): 3.96
Filter: Al 0.5 mm
Rotation Step (deg): 0.280
Output Format: 8 bit BMP
Dynamic Range: 0.000-0.140
Smoothing: 0
Beam Hardening: 0
Post Alignment: corrected
Ring Artefacts: 16

A small amount of purified MilliQ® water was carefully decanted into each sample tube. Each sample was then analysed by X-ray micro-computer tomography using a single scan, to include the water reference and the beads. The samples were then reconstructed using NRecon and calibrated against a volume of interest (VOI) of the purified water reference. A region of interest (ROI) of air and water was analysed after calibration to verify the Hounsfield calibration.

Radiopacity was reported in Hounsfield units from line scan projections across the bead. Values used for dynamic range for all samples in NRecon (thresholding): −0.005, 0.13 (minimum and maximum attenuation coefficient).

Table 2 gives the radiodensity, bismuth and solid content of microspheres prepared according to Examples 10, 11 and 13. Radiopacity data are the mean of ten line scans of each individual microsphere. Multiple microspheres were analysed for each preparation.

Example 16: Additional Bismuth Chelating Moieties

Figure 14:
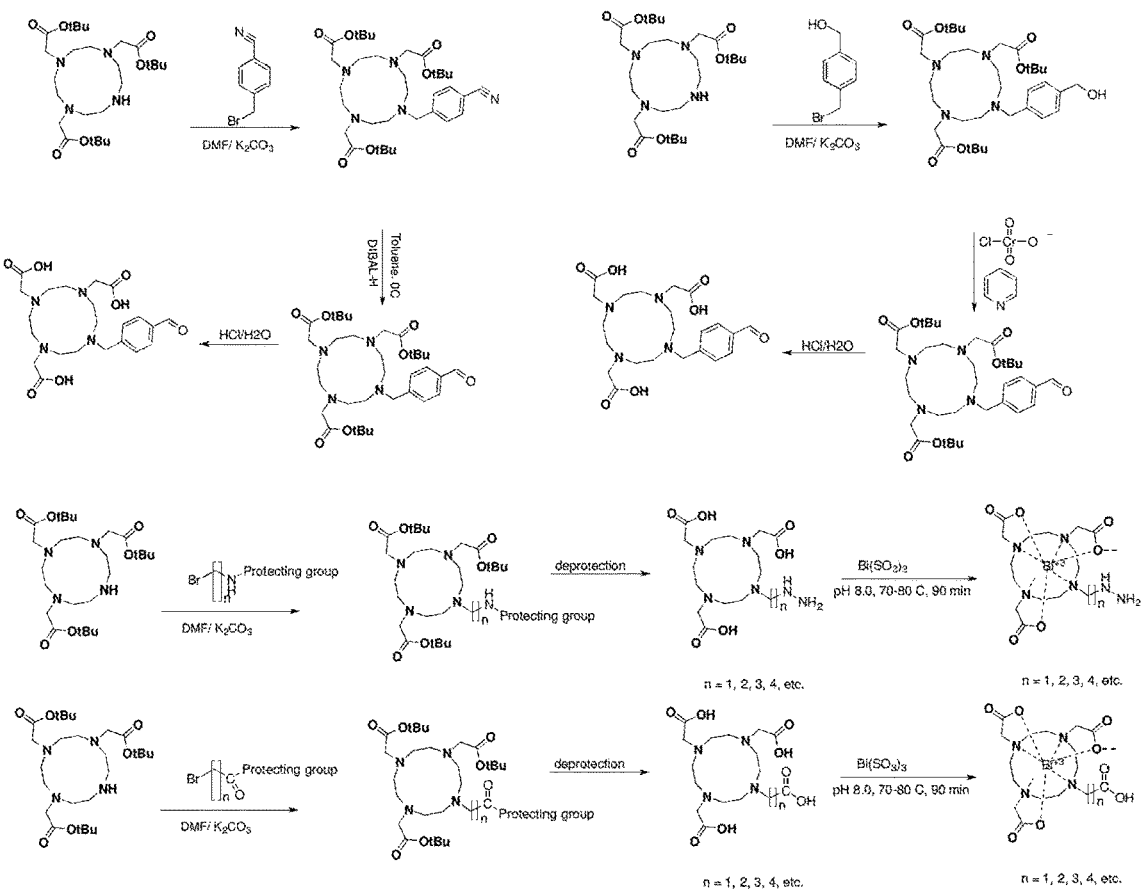
FIG. 14 shows additional bismuth chelating moieties.

FIG. 14 illustrates additional bismuth chelating moieties.

Example 17: Additional Technique for Producing Bismuth Particles

Figure 15:
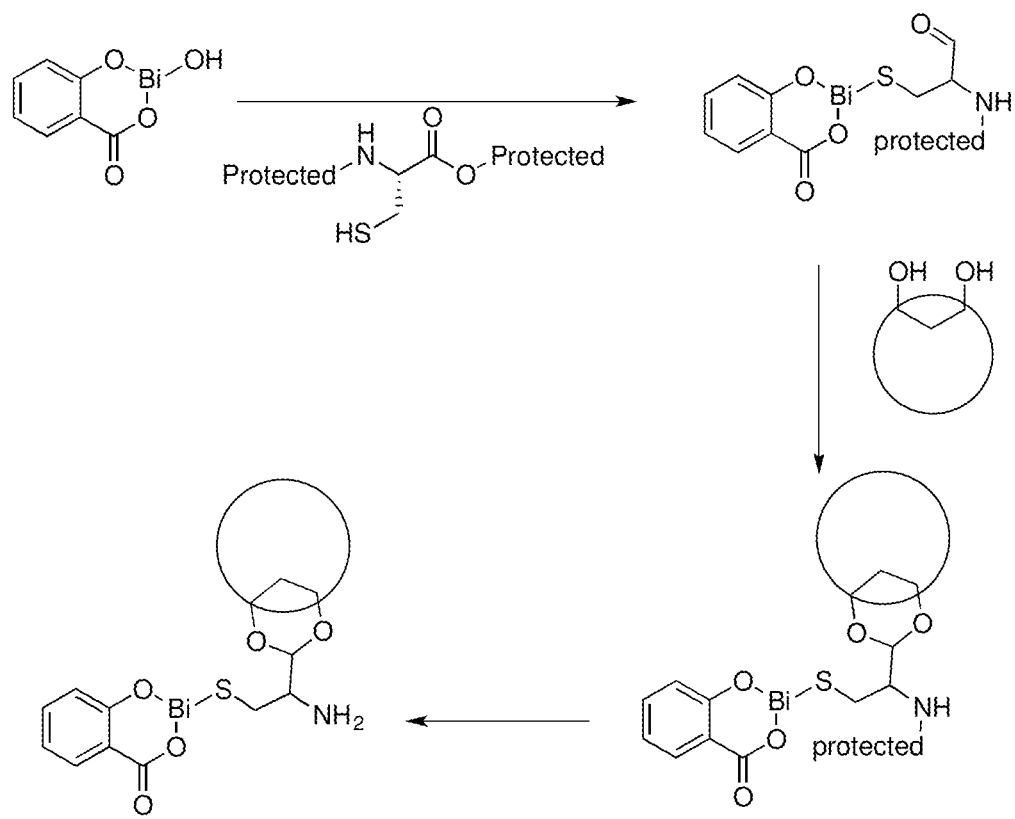
FIG. 15 shows an additional method for producing imageable bismuth particles.

FIG. 15 illustrates an additional method for making imageable bismuth particles.

Compounds are described using standard nomenclature. A dash ("-") that is not between two letters or symbols is used to indicate a point of attachment for a substituent. The suffix "yl" as used herein may indicate a group having more than one valency as indicated, for example wherein "n" is defined as 1 to 6. Otherwise, "Alkyl" means a branched or straight chain saturated aliphatic hydrocarbon group having the specified number of carbon atoms. The term $C_1$-$C_6$ alkyl indicates an alkyl group having 1, 2, 3, 4, 5, or 6 carbon atoms. Examples of alkyl include, but are not limited to, methyl, ethyl, n-propyl, isopropyl, n-butyl, 3-methylbutyl, t-butyl, n-pentyl, and sec-pentyl.

"Alkylene" means a branched or straight chain saturated aliphatic hydrocarbon group having the specified number of carbon atoms and a valence of two. Examples of alkylene groups include, but are not limited to, methylene (—($CH_2$)—) and (ethylene —($CH_2$)$_2$—). "Alkylthio" means

TABLE 2

| Sample | Ex 10 | Ex 11 | Ex 13 | A | B | C |
| --- | --- | --- | --- | --- | --- | --- |
| Average Radiopacity per bead | 2796 HU | 3996 ± 477 HU | 2648 HU | 3310 ± 763 HU | 3352 ± 610 HU | 4081 ± 865 |
| Bead solid content wt/wt* | 12.3% | 12.3% | 12.9% | — | — | — |
| Solid content of beads | 128 mg/ml | 195.4 mg/ml | 129.6 mg/ml | 190.9 mg/ml | 157.1 mg/ml | 169.7 mg/ml |
| Bismuth content dry bead | 35.0% wt/wt | 35.5% wt/wt | 26.8% wt/wt | 26.0% wt/wt | 30.9% wt/wt | 30.2% wt/wt |
| Bismuth content in wet bead | 44.6 mg/ml | 69.3 mg/ml | 34.7 mg/ml | 49.5 mg/ml | 48.6 mg/ml | 51.2 mg/ml |
| Size range | 100-160 um | 100-160 um | 355-500 um | 250-355 | 355-425 | 355-600 |

*Remainder is water.

Figure 16:
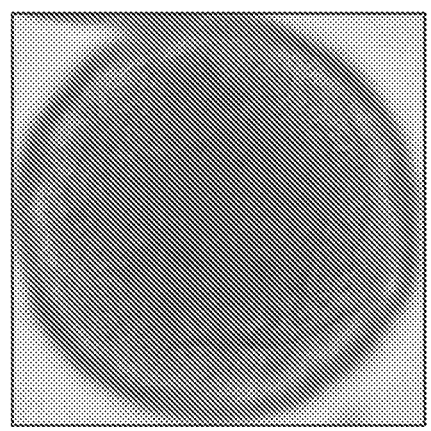
FIG. 16 shows s microspheres prepared according to Example 8 (A).
Figure 17:
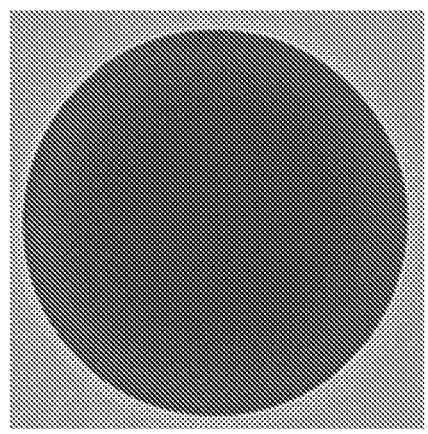
FIG. 17 shows the same microspheres as FIG. 16 carrying the same chelating group but with bismuth chelation according to Example 11 (B).

A, B and C were obtained using a modified version of Example 11 in which acidic aqueous conditions were avoided. The stage in which the the particles are washed in aqueous sodium carbonate is replaced with washes with phosphate buffered NMP and in which the particles were washed with NMP after the bismuth incorporation. Phosphate buffered saline pH 7.4 was used in place of saline and the suspension was neutralised to pH 7 with 0.1M aqueous sodium carbonate during PBS washes. Avoiding acidic aqueous conditions and using solvent conditions such as those of Example 11 leads to much cleaner microspheres and avoids the need for multiple washes to eliminate precipitated bismuth compounds within the polymer, so that the majority, if not all the bismuth within the particle is held in the chelate. FIGS. 16 and 17 compare microspheres prepared according to Example 8 with microspheres carrying the same chelating group but with bismuth chelation according to Example 11 (B).

an alkyl group as defined above attached through a sulfur linkage, i.e., a $C_2$ alkylthio is a group of the formula $CH_3CH_2S$—.

"Thio-$C_1$-$C_3$ alkylene" means an alkylene group containing a sulfur linkage either internally or at a terminus. For example, a thio-$C_1$-alkylene is a group of the formula —$SCH_2$ and a thio-$C_2$-alkylene is a group of the formula —S—$CH_2CH_2$— or —$CH_2$—S—$CH_2$—.

"Alkenyl" means a branched or straight chain aliphatic hydrocarbon group having the specified number of carbon atoms and at least one carbon-carbon double bond. For example, an ethenyl group is a $C_2$ alkenyl group of the formula $CH_2$=CH—.

"Alkenylene" means a branched or straight chain aliphatic hydrocarbon group having the specified number of carbon atoms and at least one carbon-carbon double bond, and a valence of two. For example, an ethenylene group is a $C_2$ alkenylene group of the formula —CH=CH—.

"Aryl" means an aromatic group containing only carbon in the aromatic ring or rings. Such aromatic groups may be further substituted with carbon or non-carbon atoms or groups. Aryl groups may contain one or two separate, fused, or pendant rings and from 6 to about 12 ring atoms, without heteroatoms as ring members. Aryl groups include, for example, phenyl, naphthyl, including 1-naphthyl and 2-naphthyl, and bi-phenyl. "Alkylthio" means an aryl group bound to the group it substitutes through a sulfur linkage, i.e., a $C_6$ phenylthio is a group of the formula $C_5H_5S—$.

"Arylalkyl" means an alkylene group having an aryl substituent as described above, and the number of indicated number of carbon atoms in total. For example, a benzyl group is a $C_7$ arylalkyl group.

Cycloalkyl" is a saturated hydrocarbon ring groups, having the specified number of carbon atoms, usually from 3 to 7 carbon atoms. Examples of cycloalkyl groups include cyclopropyl, cyclobutyl, cyclopentyl, or cyclohexyl as well as bridged or caged saturated ring groups such as norborane or adamantane. In the term "(cycloalkyl)alkyl," cycloalkyl and alkyl are as defined above, and the point of attachment in on the alkyl group.

Unless indicated otherwise, the compounds can optionally be substituted, provided that the synthesis or use of the compound is not substantially adversely affected. "Substituted" means that the compound or group is substituted with at least one (e.g., 1, 2, 3, or 4) substituents that can each independently be a $C_{1-9}$ alkoxy, a $C_{1-9}$ haloalkoxy, a nitro ($—NO_2$), a cyano (—CN), a $C_{1-6}$ alkyl sulfonyl (—S(=O)$_2$-alkyl), a $C_{6-12}$ aryl sulfonyl (—S(=O)$_2$-aryl) a thiol (—SH), a thiocyano (—SCN), a tosyl ($CH_3C_6H_4SO_2—$), a $C_{3-12}$ cycloalkyl, a $C_{2-12}$ alkenyl, a $C_{5-12}$ cycloalkenyl, a $C_{6-12}$ aryl, a $C_{7-13}$ arylalkylene, a $C_{4-12}$ heterocycloalkyl, and a $C_{3-12}$ heteroaryl instead of hydrogen, provided that the substituted atom's normal valence is not exceeded. The number of carbon atoms indicated in a group is exclusive of any substituents. For example —$CH_2CH_2CN$ is a $C_2$ alkyl group substituted with a nitrile.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. The term "or" is inclusive of "and/or." Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein may be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:
1. An imageable bismuth particle comprising
a hydrophilic polymer particle having an average largest diameter of 40 to 700 μm, and comprising a covalently bound compound of Formula (1) or Formula (2),

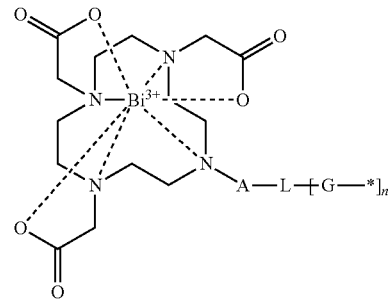

Formula (1)

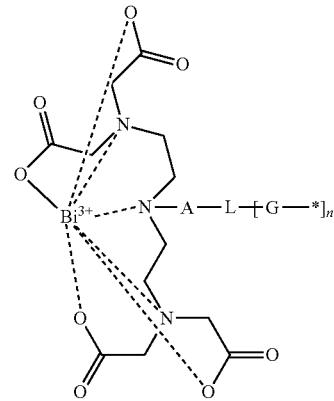

Formula (2)

wherein
A is a covalent bond or a functional group,
L is a $C_{1-12}$ linking group,
in Formula (1), G is —O—, —S—, —C(=O)—, —OC(=O)—, —C(=O)O—, —NH—, =N—, —N=N—, or —S(=O)$_2$—,
in Formula (2), G is a functional group,
provided that in Formula (1), when n is 1, then G is —O—, —S—, —C(=O)—, =N—, —N=N—, or —S(=O)$_2$—,
n is an integer corresponding to one less than the valence of L, and is 1 to 6, and
*is a point of covalent attachment to the polymer particle.
2. The imageable bismuth particle of claim 1, wherein the hydrophilic polymer particle is spherical.
3. The imageable bismuth particle of claim 1, wherein the hydrophilic polymer particle comprises polyvinyl alcohol, polyvinyl acetal, carboxymethylcellulose, hydroxyethylcellulose, polyacrylic acid, polyvinylpyrrolidone, polyacrylamide, poly(DL-lactide-co-glycolide), chitosan, alginate or a combination comprising at least one of the foregoing.

4. The imageable bismuth particle of claim 1, wherein A is a covalent bond, —C(=O)—, —N=, —N=N—, —N=N⁺=N⁻, —(CH$_2$)$_p$C(=O)NH—, â—(CH$_2$)$_p$(=O)NHC(=O)—, â—(CH$_2$)$_p$OC(=O)—, â—(CH$_2$)$_p$C(=O)O—, â—(CH$_2$)$_p$NH—, â—(CH$_2$)$_p$N=, â—(CH$_2$)$_p$N=N—, or â—(CH$_2$)$_p$NHC(=O)O—, wherein A indicates a bond to the nitrogen and p is 1 to 6, L is a linking group having a valence of n+1, and is a $C_{1-10}$ alkyl, $C_{2-10}$ alkenyl, $C_{2-10}$ alkynyl, $C_{6-10}$ aryl, $C_{3-11}$ heteroaryl, $C_{7-12}$ arylalkyl, $C_{7-12}$ alkylaryl, $C_{5-10}$ cycloalkyl, or $C_{3-9}$ heterocycloalkyl, G is —O—, —S—, —C(=O)—, —OC(=O)—, —C(=O)O—, —NH—, =N—, —N=N—, or —S(=O)$_2$—, and n is 1-3.

5. The imageable bismuth particle of claim 1, further comprising a reversibly bound active agent.

6. The imageable bismuth particle of claim 1, wherein G is —O—, —OC(=O)—, or —C(=O)O—.

7. The imageable bismuth particle of claim 1, wherein n is 2 to 6.

8. An imageable bismuth particle comprising a hydrophilic polymer particle having an average largest diameter of 40 to 700 μm, and comprising a covalently bound compound of Formula (1) or Formula (2),

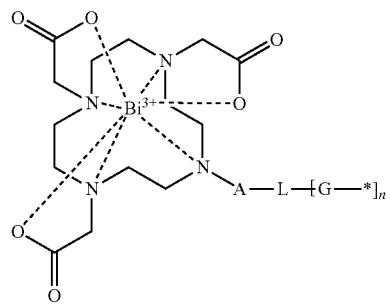

Formula (1)

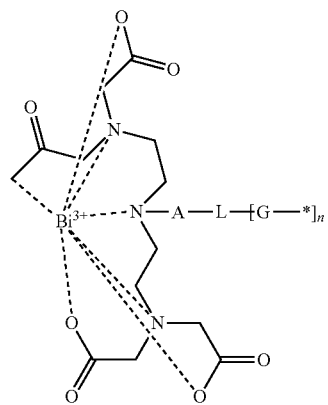

Formula (2)

wherein
A is a covalent bond or a functional group,
L is a $C_{1-12}$ linking group,
in Formula (1), G is —O—, —S—, —C(=O)—, —OC(=O)—, —C(=O)O—, —NH—, =N—, —N=N—, or —S(=O)$_2$—, in Formula (2), G is a functional group,
provided that in Formula (1), when n is 1, then G is —O—, —S—, —C(=O)—, —OC(=O)—, —C(=O)O—, =N—, —N=N—, or —S(=O)$_2$—, n is an integer corresponding to one less than the valence of L, and is 1 to 6, and

*is a point of covalent attachment to the polymer particle, wherein the ratio of the hydrophilic polymer particle to the compound of Formula (1) or Formula (2) is 0.1:1 to 1:1 (wt/wt).

9. An imageable bismuth particle comprising a hydrophilic polymer particle having an average largest diameter of 40 to 700 μm, and comprising a covalently bound compound of Formula (1a) or Formula (2a)

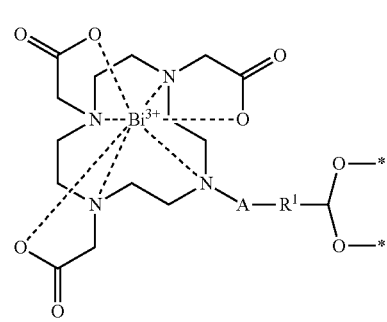

Formula (1a)

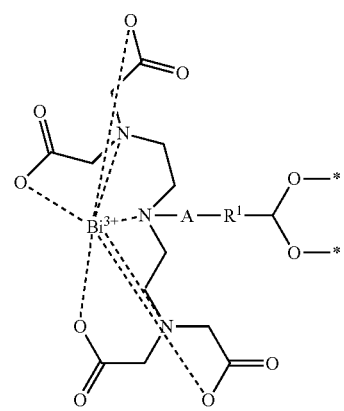

Formula (2a)

wherein
A is a covalent bond or a functional group,
$R^1$ is a bond or a $C_{1-11}$ divalent linking group, A is a covalent bond, —C(=O)—, —N=, —N=N—, —N=N⁺=N⁻, â—(CH$_2$)$_p$C(=O)NH—, â—(CH$_2$)$_p$C(=O)NHC(=O)—, â—(CH$_2$)$_p$OC(=O)—, —(CH$_2$)$_p$ C(=O)O—, â—(CH$_2$)$_p$NH—, â—(CH$_2$)$_p$N=, â—(CH$_2$)$_p$N=N—, or â—(CH$_2$)$_p$NHC(=O)O—, wherein â indicates a bond to the nitrogen and p is 1 to 6, and is a point of covalent attachment to the polymer particle.

10. The imageable bismuth particle of claim 9, wherein $R^1$ is a $C_{1-10}$ alkylene, $C_{2-10}$ alkenylene, $C_{6-10}$ arylene, $C_{3-11}$ heteroarylene, $C_{7-11}$ alkylenearylene, $C_{7-11}$ arylenealkylene, $C_{5-10}$ cycloalkylene, or $C_{3-9}$ heterocycloalkylene.

11. The imageable bismuth particle of claim 10, wherein A is a bond, —C(=O)—, or —CH$_2$C(=O)O—, and $R^1$ is a $C_{1-10}$ alkylene, $C_{6-10}$ arylene, or $C_{7-11}$ alkylenearylene.

12. The imageable bismuth particle of claim 11, wherein the compound of Formula (1a) or Formula (2a) is

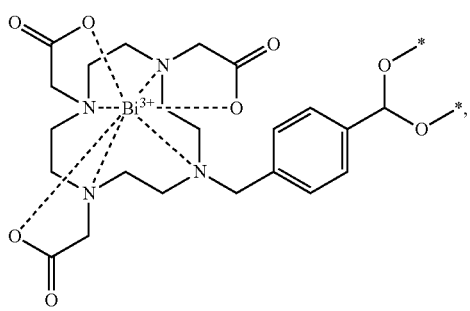

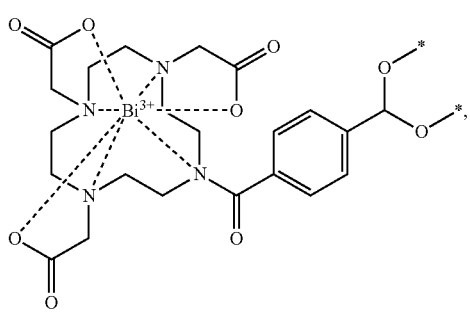

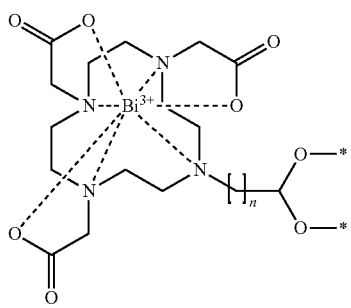

wherein n is 1 to 10,

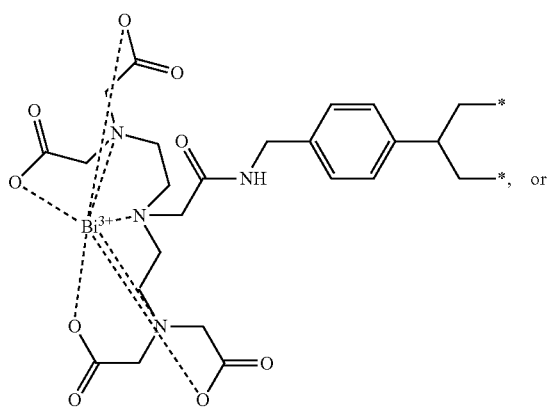

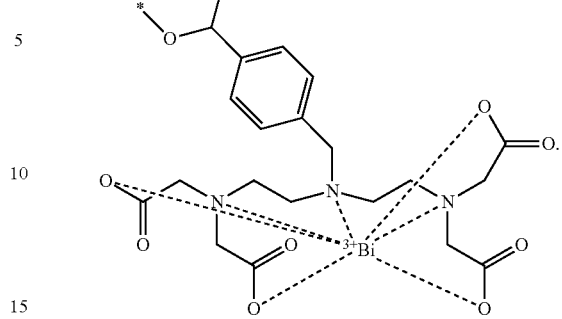

13. A method of making the imageable bismuth particle of claim 1, the method comprising
reacting a hydrophilic polymer precursor particle with a cyclen compound of Formula (3) or azanyl compound of Formula (4)

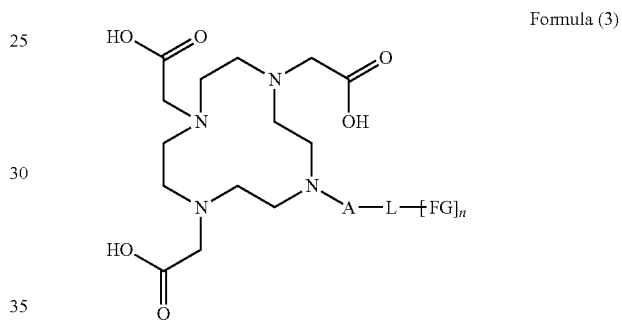

Formula (3)

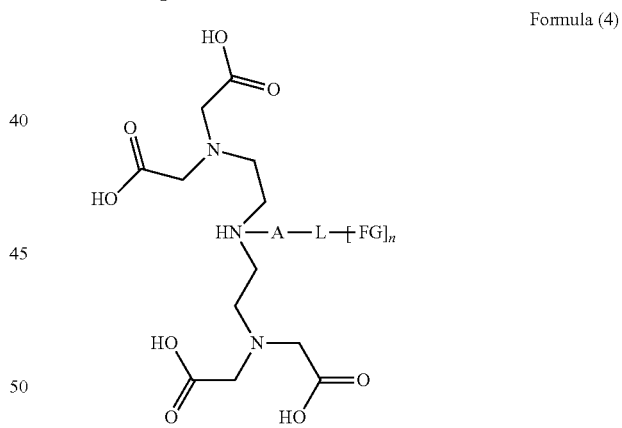

Formula (4)

under conditions effective to covalently bind the compound of Formula (3) or Formula (4) to the particle to provide a modified particle, wherein FG is a functional group reactive with a functional group of the hydrophilic polymer precursor particle, and
adding a bismuth compound to the modified particle under conditions effective to chelate the bismuth compound to the covalently bound compound of Formula (3) or Formula (4) to provide the imageable bismuth particle.

14. A method of making the imageable bismuth particle of claim 1, the method comprising
reacting a hydrophilic polymer precursor particle with a bismuth-cyclen complex of Formula (5) or a bismuth-azanyl complex of Formula (6)

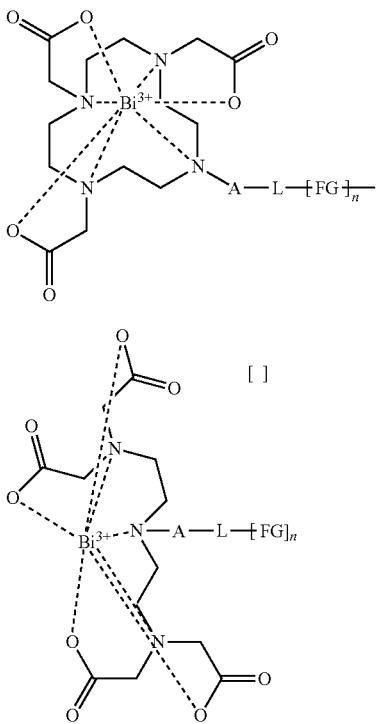

Formula (5)

Formula (6)

[ ]

under conditions effective to covalently bind the compound of Formula (5) or Formula (6) to the particle to provide the imageable bismuth particle, wherein FG is a functional group reactive with a functional group of the hydrophilic polymer precursor particle.

15. A method of imaging the imageable bismuth particles of claim 1 in a subject, comprising
intraarterially administering the imageable bismuth particles, and
imaging the imageable bismuth particles in the artery of the subject.

16. The method of claim 15, wherein intraarterial administration is performed using a catheter and/or the imageable bismuth particles are administered in a contrast agent.

17. The method of claim 15, wherein imaging comprises dual energy CT or photon counting CT.

18. The method of claim 15, wherein the imageable bismuth particles further comprise a reversibly bound active agent.

19. A method of treating a subject having a tumor, comprising intraarterially administering to an artery of the subject the imageable bismuth particles of claim 5, wherein the reversibly bound active agent is a chemotherapeutic agent, and
imaging the imageable bismuth particles in the artery of the subject, wherein the reversibly bound active agent is released from the particles into the artery.

20. The method of claim 19, wherein tumor is in the pancreas, lung, kidney, prostate, stomach, colon, head or neck of the subject.

21. The method of claim 19, wherein the subject has an intermediate stage hepatocellular carcinoma.

* * * * *